US011730349B2

(12) United States Patent
Altshuler et al.

(10) Patent No.: US 11,730,349 B2
(45) Date of Patent: Aug. 22, 2023

(54) STEERABLE MEDICAL DEVICE WITH BENDING SECTIONS AND IMPROVED CONNECTOR THEREFOR

(71) Applicant: Canon U.S.A., Inc., Melville, NY (US)

(72) Inventors: Alexander Altshuler, Cambridge, MA (US); Zachary Hamilton Haubert, Boston, MA (US)

(73) Assignee: Canon U.S.A., Inc., Melville, NY (US)

( * ) Notice: Subject to any disclaimer, the term of this patent is extended or adjusted under 35 U.S.C. 154(b) by 362 days.

(21) Appl. No.: 17/078,849

(22) Filed: Oct. 23, 2020

(65) Prior Publication Data

US 2021/0121051 A1    Apr. 29, 2021

Related U.S. Application Data

(60) Provisional application No. 62/926,352, filed on Oct. 25, 2019.

(51) Int. Cl.
*A61B 1/00* (2006.01)
*A61B 1/01* (2006.01)
(Continued)

(52) U.S. Cl.
CPC .............. *A61B 1/01* (2013.01); *A61B 1/0051* (2013.01); *A61B 1/00121* (2013.01); *A61B 34/37* (2016.02); *A61B 2034/301* (2016.02)

(58) Field of Classification Search
CPC ..... A61B 1/01; A61B 1/00121; A61B 1/0051; A61B 2034/301; A61B 2017/00292; A61B 1/0052; A61B 1/00064; A61B 1/00066; A61B 1/00105; A61B 1/00124; A62M 2017/22071; A61M 25/00; A61M 25/0136; A61M 2039/1077
(Continued)

(56) References Cited

U.S. PATENT DOCUMENTS 5,716,354 A    2/1998 Hluchy
5,803,083 A *  9/1998 Buck ...................... A61B 8/445
                                                     600/439
(Continued)

FOREIGN PATENT DOCUMENTS

WO        2018204202 A1    11/2018

*Primary Examiner* — Timothy J Neal
*Assistant Examiner* — James Edward Boice
(74) *Attorney, Agent, or Firm* — Canon U.S.A., Inc., IP Division

(57) ABSTRACT

Embodiments of a robotic medical system comprise a steerable instrument that includes a bendable body and a connector assembly configured to detachably connect the bendable body to an actuation unit. A controller is configured to control the actuation unit. The connector assembly comprises a connection receptor coupled to the actuation unit and a connecting shaft coupled to the bendable body. The connecting shaft includes a plurality of driving rods that are attached in a one-to-one correspondence to a plurality of driving wires and that detachably attach to the connection receptor. In a connected state where the bendable body is connected to the actuation unit via the connector assembly, the controller causes the actuation unit to transmit an actuating force from an actuator to a driving rod, and the driving rod actuates or moves a driving wire in a same direction as the actuating force applied by the actuator.

25 Claims, 8 Drawing Sheets

(51) Int. Cl.
*A61B 34/37* (2016.01)
*A61B 1/005* (2006.01)
*A61B 34/30* (2016.01)

(58) Field of Classification Search
USPC .................................................. 600/114, 459
See application file for complete search history.

(56) References Cited

U.S. PATENT DOCUMENTS

| | | | |
|---|---|---|---|
| 5,846,221 A * | 12/1998 | Snoke | A61M 25/0136 604/533 |
| 6,468,203 B2 | 10/2002 | Belson | |
| 6,858,005 B2 | 2/2005 | Ohline et al. | |
| 8,721,530 B2 | 5/2014 | Ohline et al. | |
| 9,144,370 B2 | 9/2015 | Kato et al. | |
| 9,629,688 B2 | 4/2017 | Robert et al. | |
| 10,105,036 B2 | 10/2018 | Julian et al. | |
| 10,292,760 B2 | 5/2019 | Haughton et al. | |
| 10,722,296 B2 | 7/2020 | Haughton et al. | |
| 10,736,490 B2 | 8/2020 | Julian et al. | |
| 10,743,750 B2 | 8/2020 | Hunter et al. | |
| 2007/0010801 A1* | 1/2007 | Chen | A61M 25/0147 606/1 |
| 2007/0135803 A1 | 6/2007 | Belson | |
| 2009/0031842 A1 | 2/2009 | Kawai et al. | |
| 2009/0247943 A1* | 10/2009 | Kirschenman | A61B 34/71 604/95.04 |
| 2010/0160730 A1* | 6/2010 | Konomura | G02B 23/2476 600/114 |
| 2011/0092776 A1 | 4/2011 | Kawai et al. | |
| 2011/0201886 A1* | 8/2011 | Gumbs | A61B 1/0016 600/118 |
| 2013/0053784 A1 | 2/2013 | Houser et al. | |
| 2013/0068372 A1* | 3/2013 | King, Jr. | B29C 65/4895 156/73.1 |
| 2015/0088161 A1 | 3/2015 | Hata et al. | |
| 2018/0243900 A1 | 8/2018 | Tanaka et al. | |
| 2018/0311006 A1 | 11/2018 | Kose et al. | |
| 2019/0015978 A1 | 1/2019 | Takagi et al. | |
| 2020/0060646 A1* | 2/2020 | Lindenroth | A61B 8/12 |
| 2020/0107898 A1* | 4/2020 | Kim | A61B 17/320016 |
| 2020/0196836 A1* | 6/2020 | De Jong | A61M 25/0136 |
| 2022/0061634 A1* | 3/2022 | Thissen | A61B 1/0052 |

\* cited by examiner

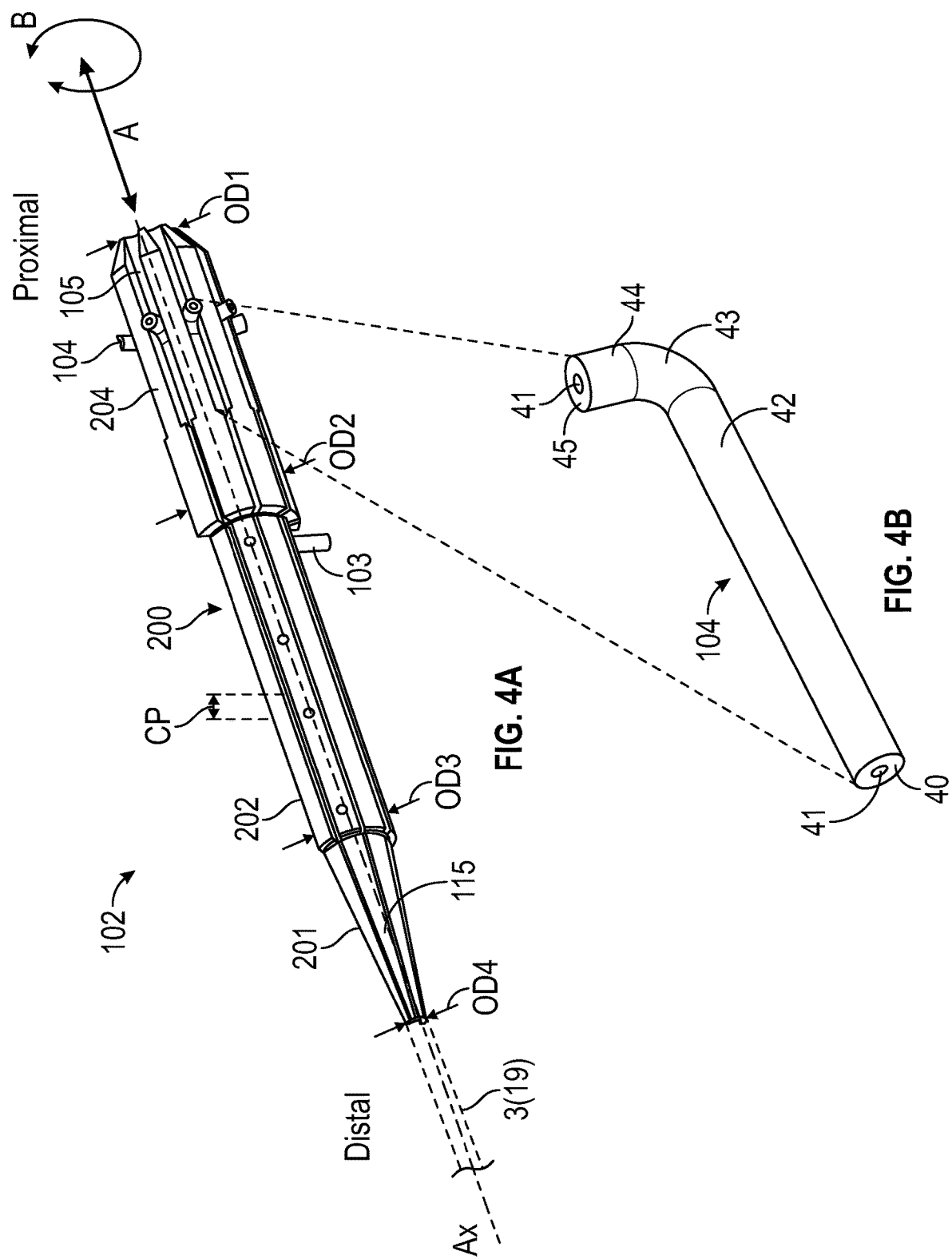

STEERABLE MEDICAL DEVICE WITH BENDING SECTIONS AND IMPROVED CONNECTOR THEREFOR

CROSS-REFERENCE TO RELATED APPLICATIONS

This application claims priority to U.S. Provisional Application Ser. No. 62/926,352, filed Oct. 25, 2019, the content of which is incorporated by reference herein in its entirety.

BACKGROUND INFORMATION

Field of Disclosure

The present disclosure generally concerns medical devices, in particular robotically steerable medical devices that are applicable to guide interventional tools and instruments, such as endoscopes and catheters.

Description of Related Art

Steerable medical devices include endoscopic surgical instruments and catheters. Some steerable medical devices use a disposable or limited-use flexible tube commonly referred to as a sleeve or sheath. This tubular sheath has a proximal end which connects to an actuator unit via an electromechanical connector, and a proximal end which is introduced into a patient's anatomy through natural orifices or small incisions. One or more tool channels extend along (e.g., inside) the sheath to allow access for imaging devices and/or end effectors located at a distal end of the sheath, and a plurality of driving wires or tendons extend along (e.g., within) the wall of the sheath to allow the actuator unit to selectively manipulate (bend) at least a portion of the sheath. This allows the steerable instrument to navigate along tortuous anatomical paths through or around and between organs of a patient's body. Driving wires or tendons are typically made of metallic material such as nickel-titanium (NiTi) alloy (nitinol), stainless still or the like. The tubular sheath has a plurality of bendable segments is typically made of biocompatible polymers, such as Polytetrafluoroethylene (PTFE)

The steerable instrument is supposed to provide flexible access with at least one curve or more to an intended lesion while retaining torsional and longitudinal rigidity so that physicians can control the end effectors located at the distal end by maneuvering a proximal end of the instrument. Steerable medical devices including endoscopes and catheters for medical examination or treatment of internal body structures are described in numerous patent-publications and non-patent publications including, for example, U.S. Pat. Nos. 6,468,203, 6,858,005, 9,629,688 and 10,105,036, the disclosures of which are hereby incorporated by reference in their entirety.

To provide minimally invasive surgical (MIS) procedures, it is desirable to minimize an outer size (outer diameter) of the bendable tubular sheath and to maximize an inner size (inner diameter) of the tool channel(s). Therefore, the bendable medical instrument preferably comprises a sheath with minimal wall thickness. At the same time, to ensure required levels of sterility, the bendable sheath must be connected and disconnected quickly from the medical system. To that end, conventional steerable medical devices as those described in the above-listed patents use a connector cartridge which includes perpendicular moving directions between the driving wires and actuation unit. The driving wires are bent in the connection cartridge. This makes the connector assembly difficult to miniaturize and creates relatively large loss of the driving forces. In addition, a connector cartridge which includes perpendicular moving directions between the driving wires and actuation unit makes it difficult to finely manipulate the bendable sheath due to backlash in the actuator or slack of the driving wires. Backlash in an actuator can be produced by a slack or non-tautly operated wire.

Accordingly, there is a need for improved connector assemblies that can simplify the connection and reduce the loss of driving forces between the actuator unit that generates the actuating forces and the plurality of elements needed to actuate the steerable instrument.

SUMMARY

Some embodiments of a medical robotic system comprise a bendable-body assembly that includes a bendable body, a driving wire, a body-lock pin, and a connection receptor, wherein the bendable-body assembly has a distal end and a proximal end, and wherein the bendable body is configured to bend at one or more bending sections; an actuation unit that is detachably connected to the bendable-body assembly via the connection receptor and that is configured to generate the bending force to bend the bendable body at the one or more bending sections; an insertion unit; and a controller that is configured to control the actuation unit.

Some embodiments of a device comprise a bendable body, a driving wire, a connecting shaft, and a connection receptor. The connecting shaft includes a driving-wire guide and a driving-wire-lock pin that is attached to the driving wire. The connection receptor includes a connection receptor body that is configured to receive the connecting shaft, includes a driving-wire-locking stage, and includes a linear slider. The driving-wire-locking stage includes a driving-wire-locking way. The driving-wire-lock pin is configured to engage the driving-wire-locking way with a rotational motion. The driving-wire-locking stage and the linear slider are configured to allow the driving-wire-locking stage to move along a longitudinal axis of the connection receptor.

Some embodiments of a device comprise a bendable body; a plurality of driving wires; and a connecting shaft that includes a plurality of driving-wire-lock pins that are attached to the driving wires, wherein the connecting shaft is configured to be detachably connected to a connection receptor, and wherein the driving-wire-lock pins are configured to move along a longitudinal axis of the connecting shaft.

Some embodiments of a device comprise a connection receptor body that is configured to receive a connecting shaft; a linear slider; and a driving-wire-locking stage, wherein the driving-wire-locking stage is configured to engage a driving-wire-lock pin of a connecting shaft with a rotational motion of the connecting shaft relative to the connection receptor.

BRIEF DESCRIPTION OF THE DRAWINGS

FIG. 4A illustrates an example embodiment of a connecting shaft 102 according to the present disclosure. FIG. 4B illustrates an example embodiment of a driving rod 104 according to the present disclosure.

DESCRIPTION

Figure 1A:
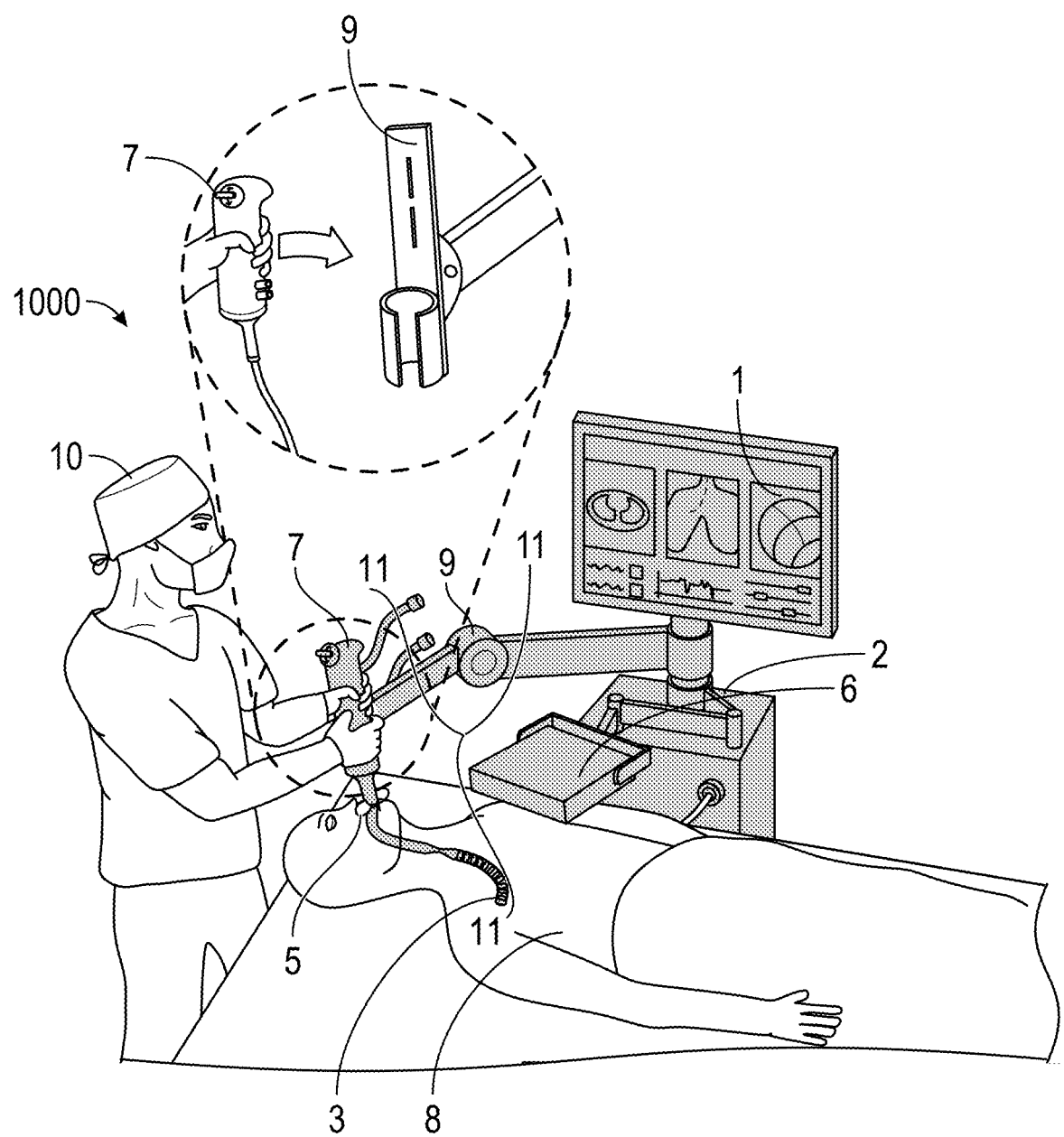
FIG. 1A illustrates an example embodiment of a medical system 1000 including a steerable medical device 11 in an applicable medical environment thereof.

The following paragraphs describe certain explanatory embodiments. Other embodiments may include alternatives, equivalents, and modifications. Additionally, the explanatory embodiments may include several features, and a particular feature may not be essential to some embodiments of the devices, systems, and methods that are described herein.

Throughout the figures, where possible, the same reference numerals and characters, unless otherwise stated, are used to denote like features, elements, components or portions of the illustrated embodiments. In addition, while the subject disclosure is described in detail with reference to the enclosed figures, it is done so in connection with illustrative exemplary embodiments. It is intended that changes and modifications can be made to the described exemplary embodiments without departing from the true scope and spirit of the subject disclosure as defined by the appended claims. Although the drawings represent some possible configurations and approaches, the drawings are not necessarily to scale and certain features may be exaggerated, removed, or partially sectioned to better illustrate and explain certain aspects of the present disclosure. The descriptions set forth herein are not intended to be exhaustive or otherwise limit or restrict the claims to the precise forms and configurations shown in the drawings and disclosed in the following detailed description.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached", "coupled" or the like to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown in one embodiment can apply to other embodiments. It will also be appreciated by those of skill in the art that references to a structure or feature that is disposed "adjacent" to another feature may have portions that overlap or underlie the adjacent feature.

The terms first, second, third, etc. may be used herein to describe various elements, components, regions, parts and/ or sections. It should be understood that these elements, components, regions, parts and/or sections are not limited by these terms of designation. These terms of designation have been used only to distinguish one element, component, region, part, or section from another region, part, or section. Thus, a first element, component, region, part, or section discussed below could be termed a second element, component, region, part, or section merely for purposes of distinction but without limitation and without departing from structural or functional meaning.

As used herein, the singular forms "a", "an", and "the" are intended to include the plural forms as well, unless the context clearly indicates otherwise. It should be further understood that the terms "includes" and/or "including", "comprises" and/or "comprising", "consists" and/or "consisting" when used in the present specification and claims, specify the presence of stated features, integers, steps, operations, elements, and/or components, but do not preclude the presence or addition of one or more other features, integers, steps, operations, elements, components, and/or groups thereof not explicitly stated. Further, in the present disclosure, the transitional phrase "consisting of" excludes any element, step, or component not specified in the claim. It is further noted that some claims or some features of a claim may be drafted to exclude any optional element; such claims may use exclusive terminology as "solely," "only" and the like in connection with the recitation of claim elements, or it may use of a "negative" limitation.

The term "about" or "approximately" as used herein means, for example, within 10%, within 5%, or less. In some embodiments, the term "about" may mean within measurement error. In this regard, where described or claimed, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range, if recited herein, is intended to include all sub-ranges subsumed therein. As used herein, the term "substantially" is meant to allow for deviations from the descriptor that do not negatively affect the intended purpose. For example, deviations that are from limitations in measurements, differences within manufacture tolerance, or variations of less than 5% can be considered within the scope of substantially the same. The specified descriptor can be an absolute value (e.g. substantially spherical, substantially perpendicular, substantially concentric, etc.) or a relative term (e.g. substantially similar, substantially the same, etc.).

The present disclosure generally relates to medical devices, and it exemplifies embodiments of a catheter and/or an optical probe which may be applicable to an imaging apparatus (e.g., an endoscope). The imaging apparatus may image using a miniature camera based on chip-on-tip (COT) technology, or may provide some other form of imaging such as spectrally encoded endoscopy (SEE) imaging technology (see, e.g., U.S. Pat. Nos. 10,288,868 and 10,261, 223). In some embodiments, the imaging apparatus may include an optical coherence tomographic (OCT) apparatus, a spectroscopy apparatus, or a combination of such apparatuses (e.g., a multi-modality imaging probe).

The embodiments of the optical probe and portions thereof are described in terms of their positon/orientation in a three-dimensional space. As used herein, the term "position" refers to the location of an object or a portion of an object in the three-dimensional space (e.g., three degrees of translational freedom along Cartesian X, Y, Z coordinates); the term "orientation" refers to the rotational placement of an object or a portion of an object (three degrees of rotational freedom—e.g., roll, pitch, and yaw); the term "posture" refers to the position of an object or a portion of an object in at least one degree of translational freedom and to the orientation of that object or portion of object in at least one degree of rotational freedom (up to a total six degrees of freedom); the term "shape" refers to a set of posture, positions, and/or orientations measured along the elongated body of the object. As it is known in the field of medical devices, the terms "proximal" and "distal" are used with reference to the manipulation of an end of an instrument extending from the user to a surgical or diagnostic site. In this regard, the term "proximal" refers to the portion of the instrument closer to the user, and the term "distal" refers to the portion of the instrument further away from the user and closer to a surgical or diagnostic site.

As used herein the term "catheter" generally refers to a flexible and thin tubular instrument made of medical grade material designed to be inserted through a narrow opening into a bodily lumen (e.g., a vessel) to perform a broad range of medical functions. The catheter may be solely an imaging apparatus or it may comprise tools for use in therapeutic or diagnostic procedures. The more specific term "optical catheter" refers to a medical instrument comprising an elongated bundle of one or more flexible light conducting fibers disposed inside a protective sheath made of medical grade material and having an optical imaging function. A particular example of an optical catheter is fiber optic catheter which comprises a sheath, a coil, a protector and an optical probe. In some applications a catheter may include a "guide catheter" which functions similarly to a sheath.

As used herein the term "endoscope" refers to a rigid or flexible medical instrument which uses light guided by an optical probe to look inside a body cavity or organ. A medical procedure, in which an endoscope is inserted through a natural opening, is called an endoscopy. Specialized endoscopes are generally named for how or where the endoscope is intended to be used, such as the bronchoscope (mouth), sigmoidoscope (rectum), cystoscope (bladder), nephroscope (kidney), bronchoscope (bronchi), laryngoscope (larynx), otoscope (ear), arthroscope (joint), laparoscope (abdomen), and gastrointestinal endoscopes.

In the present disclosure, the terms "optical fiber", "fiber optic", or simply "fiber" refers to an elongated, flexible, light conducting conduit capable of conducting light from one end to another end due to the effect known as total internal reflection. The terms "light guiding component" or "waveguide" may also refer to, or may have the functionality of, an optical fiber. The term "fiber" may refer to one or more light conducting fibers. An optical fiber has a generally transparent, homogenous core, through which the light is guided, and the core is surrounded by a homogenous cladding. The refraction index of the core is larger than the refraction index of the cladding. Depending on design choice some fibers can have multiple claddings surrounding the core.

Some medical bendable instruments provide flexible access (e.g., access with one or more curves) to an intended lesion or other interior site while retaining torsional and longitudinal rigidity so that physicians can control the end effectors located at the distal end (the end closest to the interior site) by operating a proximal end (the end farthest from the interior site and closest to the physician) of the instrument.

To access deep-seated lesions and other sites, some medical bendable instruments are designed (1) to minimize an outer size (cross-sectional diameter) of the medical bendable instruments and (2) to maximize a size (cross-sectional diameter) of the tool channels. Therefore, medical bendable instruments may comprise a sheath that has a minimal wall thickness.

Furthermore, some medical bendable instruments are robotized medical instruments that include a bendable body with driving wires actuated in push and pull directions to cause portions of the bendable body to bend.

First, structural components of a robotic medical system 1000 comprising a bendable body 3 detachably attached to an actuation unit 7 via a connector assembly 5 will be described with reference to FIG. 1A, FIG. 1B, and FIG. 2A-2C. The robotic medical system 1000 can include a continuum or multi-segment robot configured to form a continuously curved geometry by actuating one or more bending sections of the bendable body 3. An example of a continuum robot is a snake-like endoscopic device, as described in applicant's previously published U.S. Pat. No. 9,144,370, and patent application publications US 2015/0088161, US 2018/0243900, US 2018/0311006 and US 2019/0015978, which are incorporated by reference herein for all purposes.

Figure 1B:
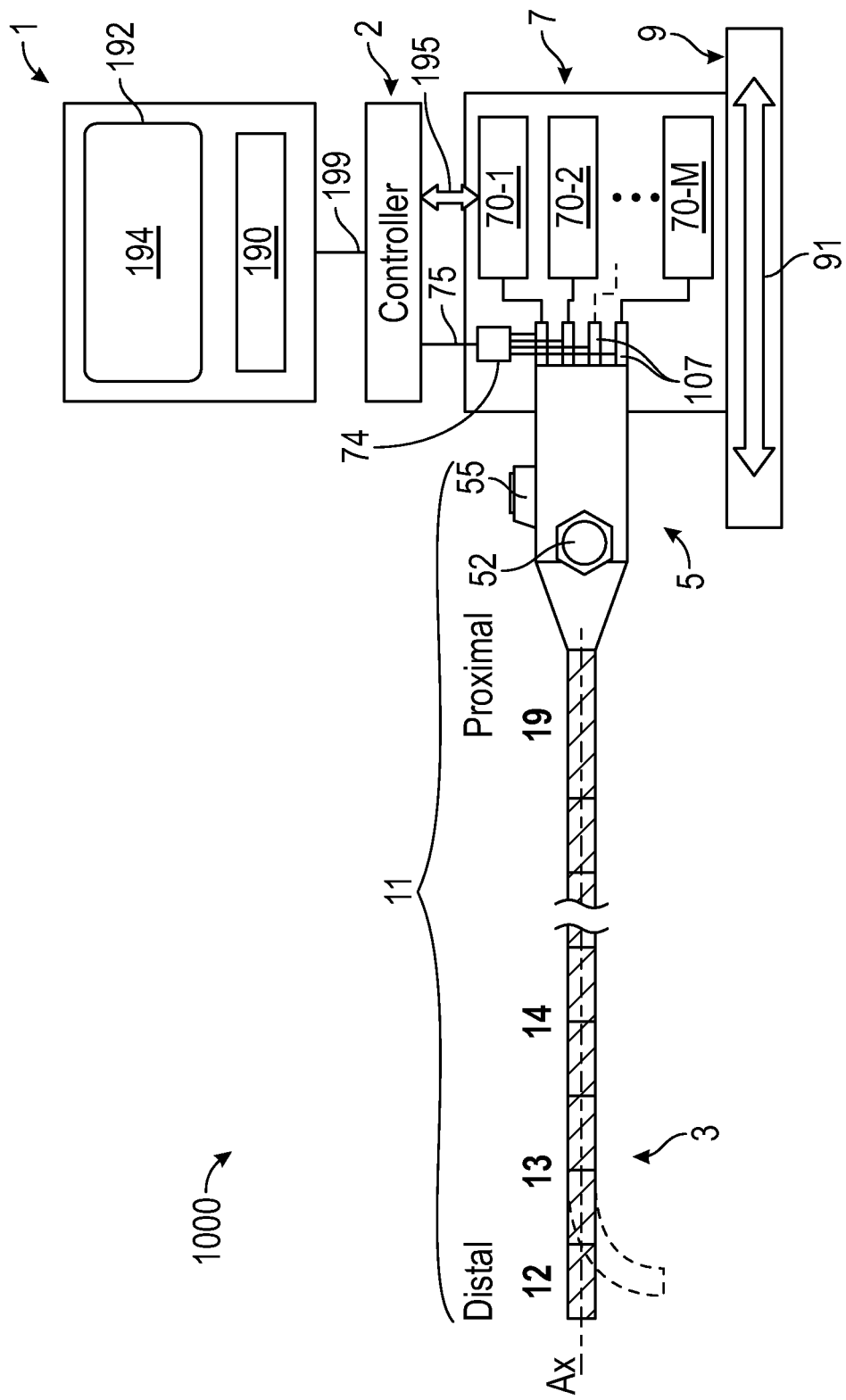
FIG. 1B illustrates an example embodiment of the medical system 1000 in bock diagram form.

<FIG. 1A-1B Robotic Medical System>

FIG. 1A illustrates an example embodiment of a medical system 1000 comprising a steerable instrument 11 (steerable medical device) configure to treat a patient 8 under operations and commands of a user (e.g., a physician) 10. The medical system 1000 includes at least a navigation system 1, a controller system 2, and the steerable instrument 11. The steerable instrument 11 includes an actuation unit 7 and a bendable body 3, which are connected to each other by a connector assembly 5. The actuation unit 7 is configured to be detachably mounted on an insertion unit 9, such as a robotic support platform, as shown in the inset detail of FIG. 1A.

FIG. 1B illustrates an example embodiment of the medical system 1000 in functional block diagram. The steerable instrument 11 can be configured for a number of medical applications and/or industrial applications. Under medical applications, the steerable instrument 11 can be configured as a robotic endoscope, a steerable catheter, a surgical introducer sheath or sleeve that uses principles of kinematic (robotic) navigation for guiding a medical tool through tortuous bodily lumens. Robotic endoscopes can be used for a variety of different diagnostic and interventional procedures, including colonoscopy, bronchoscopy, laparoscopy and video endoscopy. In the case of a video endoscope, the steerable instrument 11 would be configured with a miniature video camera, such as a CCD or CMOS camera, positioned at the distal portion of the bendable body 3.

FIG. 1B shows the steerable instrument 11 having a distal steerable section (bendable body 3) made of the multiple bending segments (bending sections 12, 13, 14), and a non-bending proximal part 19 which are arranged along a longitudinal axis (Ax). The steerable instrument n is controlled by a robotic controller system 2 via the actuation unit 7, which is connected to the proximal part 19 of the bendable body 3 by a connector assembly 5. The actuation unit 7 may be mounted on an insertion unit 9. The actuation unit 7 can include any force generating device and a mechanical element respectively used to generate and transmit sufficient actuating force for bending at least one bending section of the bendable body 3. In that regard, actuation unit 7 may include any device capable of generating and transmitting an actuating force including, for example, a mechanical force, hydraulic force, magnetic force, or pneumatic force. The insertion unit 9 may include, for example, a robotic arm and a linear stage 91 which serves to guide the actuation unit 7 and the bendable body 3 in a moving direction (typically linear movement) for insertion and/or retraction of the steerable instrument 11 with respect to the patient 8. The controller system 2 generally includes a microcontroller or other digital signal processor (DSP) device along with suitable software, firmware and peripheral hardware, which are generally known per se to persons having ordinary skill in the art. The controller system 2 can be part of, or is connected to, the navigation system 1 (e.g., a computer or system console). The navigation system 1 includes the necessary software (computer-executable code, programs and applications) executable by a processor or central processing unit (CPU) 190, according to a user's interactions with the system via a user interface 194, to control the steerable instrument u. The user interface 194 may include, for example, a display device 192 which may include a graphical user interface (GUI) and/or a pointing device and keyboard (not shown), or touchscreen.

The navigation system 1, the controller system 2, and the actuation unit 7, are operably connected to each other by a network connection or a cable bundle 199 and a data bus system 195. Among other functions, the navigation system 1 can provide a surgeon or other user with a GUI and other information displayed in the image display device 192, so that the user can interact and remotely operate the steerable instrument 11.

The controller system 2 is configured to control the actuation unit 7 which includes a plurality of actuating motors (or actuators) 70-1, 70-2 . . . , 70-M. The number of actuators 70 or motors 70 will depend on the design of the actuation unit 7, and it can include a single (one) actuator or motor that can actuate all driving wires independently, or it could include a number of actuators or motors equal to a number of driving wires 115 that can actuate each driving wire individually.

The controller system 2 may also include or be connected to one or more sensors 74. Sensors 74 can include a strain sensor and/or a position sensor which are configured to detect and/or measure compressive or tensile forces exerted on the driving wires of the steerable instrument 11. Sensors 74 may output a signal 75 corresponding to an amount of compressive or tensile force (an amount of strain) being applied to a driving wire at any given point in time. The signals 75 from the sensors 74 (strain sensor and/or position sensor) for each driving wire are fed into the controller system 2 to control each actuator individually. In this manner, each driving wire can be actively controlled, by a feedback loop, to implement appropriate shaft guidance for navigating the steerable instrument 11 through intraluminal tortuous paths of a patient's anatomy.

Figure 2A:
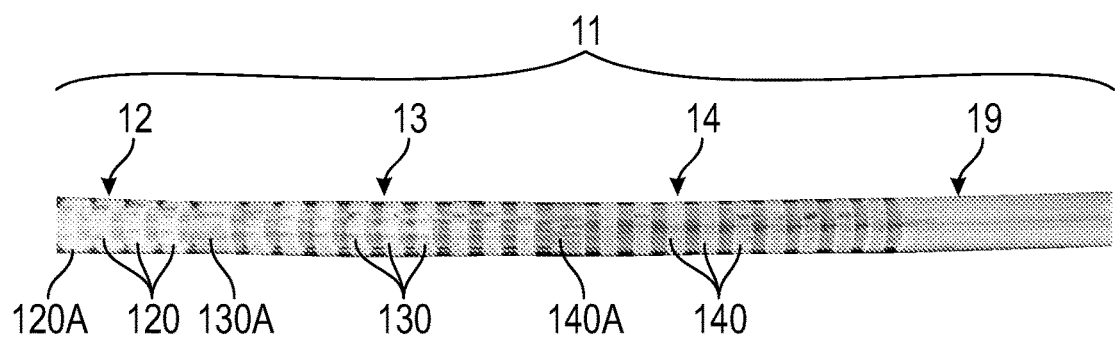
FIG. 2A, FIG. 2B and FIG. 2C illustrate structural details of a bendable body 3, according to embodiments of the present disclosure.
Figure 2B:
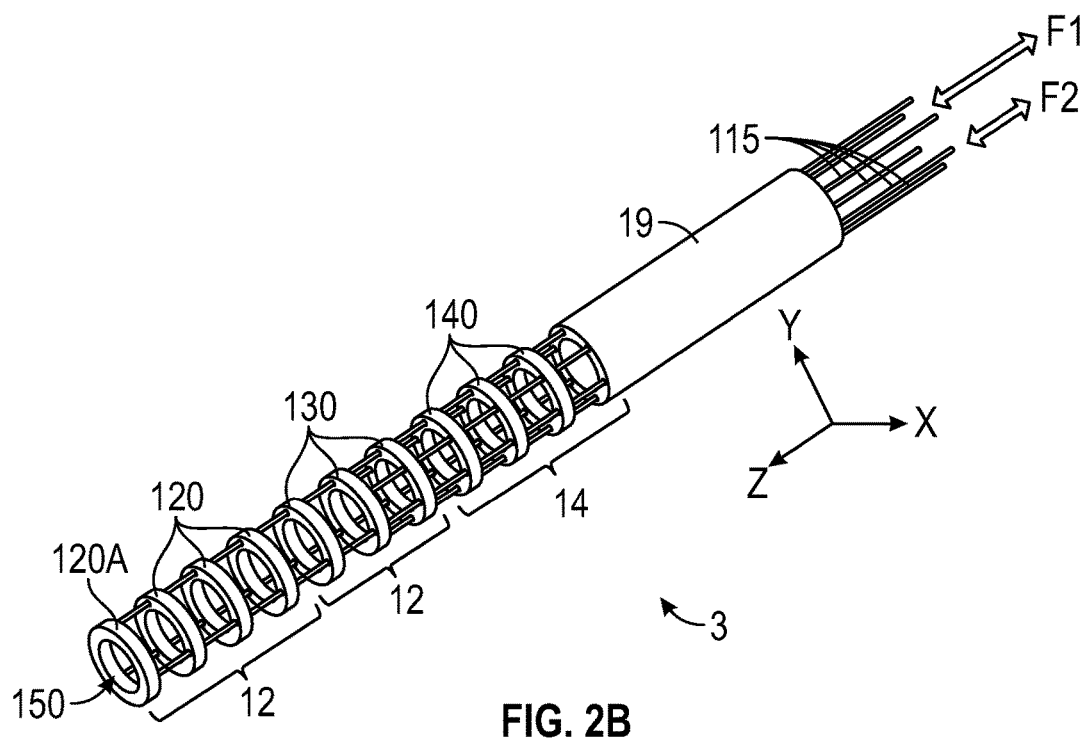
Figure 2C:
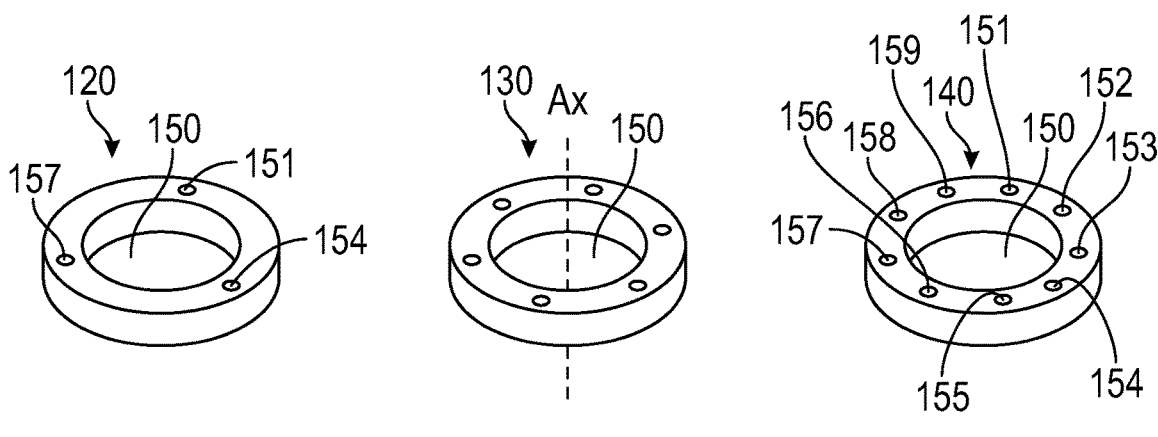

<FIG. 2A-2C: Bendable Body>

FIG. 2A, FIG. 2B, and FIG. 2C illustrate additional details of the steerable instrument 11, in particular the bendable body 3, according to an embodiment of the present disclosure. FIG. 2A is a photograph of a prototype bendable body 3 including a non-bending proximal part 19, a plurality of bending segments comprising a proximal bending section 14, a middle bending section 13, and a distal bending section 12. The bendable body 3 is a tubular structure having a stiff non-bending part, and one or more bending sections, the tubular structure comprising an outer surface and an inner surface defining a wall, the inner surface defines a tool channel 150 and the wall has a plurality of wire conduits through which driving wires 115 are moved by an actuating force to bend the bendable body 3. FIG. 2B illustrates a 3D graphical representation of the bendable body 3 configured to be actuated by a plurality of driving wires 115. FIG. 2C shows graphical representations of annular shaped (annulus) wire-guiding members having a central opening or tool channel 150 and wire conduits formed in the wall of the guiding members.

As shown in FIG. 2A and FIG. 2B, each bending section 12, 13, and 14 of the bendable body 3 includes a plurality of ring-shaped wire-guiding members, while the non-bending proximal part 19 is made of a single piece tubular component. Here, the tubular shaped proximal art 19 and the ring-shaped wire-guiding members can be made of biocompatible polymer materials, such as polyether block amide copolymer (e.g., Pebax® brand by Arkema) is a very common polymer used in the fabrication of catheter shafts. However, in the present application, other medical-grade thermoplastic polyurethane (TPU) and thermoplastic elastomer (TPE) materials are also applicable as tubing extrusion materials for medical catheter and endoscope devices that demand precision and consistency. Commonly known catheter tubing materials may include PVC, HDPE, Polyurethane, Nylon, PEBAX®, FEP, PFA, ETFE, PTFE (liners), PEEK, TPE, Grilamid®, among others.

Each wire-guiding member has a predetermined number of wire conduits (or thru-holes) through which the driving wires pass. The number of wire conduits in each wire-guiding member depends on the bending section in which the wire-guiding member is arranged. The distal bending section 12 includes a plurality of wire-guiding members 120; the middle bending section 13 includes a plurality of wire-guiding members 130; and the proximal bending section 14 includes a plurality of wire-guiding members 140. The distal bending section 12 is joined to the middle bending section 13 by an anchor member 130A; and the middle bending section 13 is connected to the proximal bending section 14 by an anchor member 140A. The proximal part 19 is a non-bending section, but it does include the plurality of wire conduits extending through the wall. Here, it should be noted that wire conduits are not limited to thru-holes or conduits within the wall itself. In some embodiments, the wire conduits can be formed on the outer surface of the tubular structure in at least part of the bendable body 3.

FIG. 2B shows the bendable body 3 having a central opening or tool channel 150 in a relaxed or non-actuated state. As shown in FIG. 2B, a plurality of driving wires 115 pass through the proximal part 19, advance through wire conduits of wire-guiding members 140 of the proximal bending section 14, pass through wire conduits of wire-guiding members 130 of the middle bending section 13, and pass through wire conduits of wire-guiding members 120 of the distal bending section 12. Each bending section is actuated by a set of antagonistic driving wires 115 which operate by a pulling or pushing force (an actuating force) to bend each bending section independently. Forces F1 and F2 of different magnitude can be applied in the lengthwise direction of each driving wire to bend the various bending sections in desired directions. A combination of forces F1 and F2 can also be applied to bend a bending section in additional directions. To that end, a first set of driving wires 115 may be anchored at an anchor member 120A at the distal end of the distal section 12, a second set of driving wires 115 may be anchored at the anchor member 130A of the middle bending section 13, and at a third set of driving wires 115 may be anchored at the anchor member 140A of the proximal bending section 14. For the sake of illustration, anchor members 130A and 140A are not labeled in FIG. 2B.

According to one example embodiment, 3 driving wires 115 may be used to actuate each bending section. In that case, the distal ends of the driving wires 115 in the first set of driving wires can be anchored to anchor member 120A, the second set of driving wires can be anchored to the anchor member 130A, and the third set of driving wires can be anchored to the anchor member 140A. In such example, nine driving wires 115 will pass through the proximal part 19 of the bendable body 3. At each anchor member, it may be advantageous to arrange (to anchor) the driving wires 115 around the circumference of each anchor member at strategic locations so as to actuate each bending section independently in a desired direction. For example, each driving wire 115 can be anchored at equal intervals around the anchor member, e.g., when each bending section is actuated by 3 wires, the driving wires would be anchored at 120-degree intervals to be able to actuate each bending section in substantially any direction.

FIG. 2C shows one wire-guiding member 120, one wire-guiding member 130, and one wire-guiding member 140. The wire-guiding member 120 includes three wire guiding conduits (151, 154, 157); the wire-guiding member 130 includes six wire guiding conduits (152-153, 155-156, 158-159); and the wire-guiding member 140 includes nine wire guiding conduits (151, 152, 153, 154, 155, 156, 157, 158 and 159). In this manner, nine driving wires 115 can be arranged through the tubular wall in the proximal part 19 of bendable body 3. Then, the driving wires are distributed and anchored for each bending section. The anchoring members 120A, 130A and 140A are of substantially similar structure as the corresponding wire-guiding members 120-140. All wire-guiding members and anchoring members include a central opening or tool channel 150, and have a predetermined number of thru-holes (wire-guiding conduits) arranged around the tool channel 150 substantially parallel to the instrument axis Ax. The number of thru-holes in each wire-guiding member and anchoring member depends on the bending section to which each member belongs.

Referring back to FIG. 1A and FIG. 1B, the connector assembly 5 provides an electromechanical interface between the bendable body 3, the actuators in actuation unit 7. For example, the connector assembly 5 may provide mechanical, electrical, and/or optical connections, and other data/digital connections for interfacing the steerable instrument 11 with the controller system 2 and the navigation system 1. The connector assembly 5 may also provide an access port 55 which can be used by a surgeon or other operator to insert instruments or end effectors through the tool channel 150. For example, the access port 55 can be used to insert small instruments, such as small forceps, needles, or electrocautery instruments and the like. In addition, the connector assembly 5 may include one or more dials or control wheels 52 for manual control (bending or steering) of at least one section of the bendable body 3. In some embodiments, the bendable body 3 may include more that one tool channel 150, where at least one of those channels can be used for passing liquid and/or gaseous fluids, and another channel can be used for tools or imaging devices.

In operation, the navigation system 1 and the controller system 2 are communicatively-coupled via the data bus 199 to transmit and receive data to and from each other. The navigation system 1 is also connected to, and communicates with, external equipment such as a computed tomography (CT) scanner, a fluoroscope imager, an image server (not shown in FIG. 1A), etc., which are external of the medical system 1000. The image server may include, but is not limited to, a DICOM™ server connected to a PACS (Picture Archiving and Communication System) or medical imaging system which may include, but is not limited to, one or more of the CT scanner, a magnetic resonance imaging (MRI) scanner, or a fluoroscope, etc. The navigation system 1 processes data provided by the controller system 2, data provided by images stored on the image server, or data provided by images from the CT scanner or the fluoroscope. The navigation system 1 displays images and other medical information in an image display device 194 to aid the user 10 in performing a medical procedure.

For a medical procedure where the steerable instrument 11 will be used, medical images (e.g., from the CT scanner) are pre-operatively provided to the navigation system 1. With the navigation system 1, a clinical user creates an anatomical computer model from the images. In the particular example embodiment of FIG. 1A, the anatomy is lung airways. From the chest images of the CT scanner, the clinical user can segment the lung airways for clinical treatments, such as a biopsy. After the navigation system 1 generates a map of the lung airways, the user can also use the navigation software system to create a plan to access a lesion for the biopsy. The plan includes the target lesion and a trajectory (navigation path) through the airways to insert the bendable body 3 of the steerable instrument 11.

The controller system 2 includes firmware, control circuitry and peripheral hardware to control the steerable instrument 11, the insertion unit 9, and field generator 6 (e.g., an EM field generator). The controller system 2 is communicatively coupled with the actuation unit 7, the insertion unit 9, the field generator 6, and a man-machine interface (e.g., a gamepad controller not shown in FIG. 1A-FIG. 1B). In this manner, the controller system 2, in coordination with the navigation system 1, controls the overall functions of the steerable instrument 11 and the insertion unit 9.

The steerable instrument 11 includes the bendable body 3, the connector 5, and the actuation unit 7. The actuation unit 7 is configured to bend one or more bending sections of the bendable body 3 via the connector assembly 5 according to commands from the controller system 2, and based on a navigation plan provided by navigation system 1.

The steerable instrument 11 is detachably attached to the insertion unit 9 via the actuation unit 7. Therefore, controller system 2 can synchronize the operation of the actuation unit 7 with the operation of the insertion unit 9 according to a connected state (ON-state) or a disconnected state (OFF-state) of the actuation unit 7. Specifically, the insertion unit 9 includes an articulated arm system and a linear stage 91 configured to hold the actuation unit 7 for robotic control during a medical procedure. However, at least part of the medical procedure may not require use of the insertion unit 9.

More specifically, for a given medical procedure, the user must follow a workflow which defines a process for insertion and controlled navigation. In such a workflow, initially, a patient preparation step occurs. For example, in a bronchoscopy procedure, the user (an endoscopist) first prepares the patient by manually inserting an endotracheal guide tube into a patient's mouth. Then, the user attaches a new and sterile bendable body 3 to the actuation unit 7 which is already attached to the insertion unit 9. Next, an auto-calibration process occurs in the steerable instrument 11, where the system can calibrate initial positions of the driving wires 115 to a straight catheter position, so that navigation can start from a known reference frame. Subsequently, the user may remove the actuation unit 7 and bendable body 3 from the insertion unit 9, and manually inserts the bendable body 3 to a predetermined location within the patient using manual steering controls. For example, for a bronchoscopy, the user may manually insert the bendable body 3 to the first carina of the patient while steering the tip of the bendable body 3 with a control knob of the actuation unit 7 or a man-machine interface. After reaching the predetermined location in the patient, the user attaches the actuation unit 7 back onto the insertion unit 9. Thereafter, the controller system 2 enters robotic control mode so that the user can navigate the tip of the bendable body 3 to the desired target location using the on-screen images and a pre-established navigation plan. In this manner, the controller system 2 can change the operation mode of the steerable instrument 1 based on whether bendable body 3 is attached to the actuation unit 7 (ON-state) or not (OFF-state).

In the ON-state, the bendable body 3 of the steerable instrument 11 is configured to be inserted into an anatomy of the patient 8 (e.g., inside a lung of a patient 8) under robotic control. To that end, the physician 10 can enter an input value to the controller system 2 via the man-machine interface (e.g., a joystick, a keyboard). According to the input value, the controller system 2 moves the actuation unit 7, or the insertion unit 9, or both to reflect the physician's intention for control. The bendable body 3 can reach the vicinity of a target lesion or other target site, and can guide medical tools (e.g., biopsy tools) by using one or more tool channels 150 in the bendable body 3.

According to one embodiment, either during insertion or retraction of the steerable instrument 11, the controller system 2 may control the linear stage 91 of insertion unit 9 to move the bendable body 3 along the center line of a lumen (e.g., an airway) in a desired trajectory followed by active control of the bending sections. This is similar to known shaft guidance techniques used to control robotic guided catheters or endoscopes with the goal of forcing the flexible shaft of the bendable body 3 to keep to a desired trajectory. In one example, when using the navigation system 1, the steerable instrument 11 is robotically controlled to advance the bendable body 3 through a lumen while sensors 84 measure the actuation force, insertion depth, the angulations of user-controlled steerable segments, etc., to obtain trajectory information. The trajectory information is stored in a memory of the system and continuously updated. After a short advance in insertion or retraction distance, the shape of the bendable body 3 is corrected by adjusting (rotating or bending) one or more of the bending sections in such a way that the new shape closely matches the desired trajectory. This process is repeated until a target area is reached. The same process is applied when the steerable instrument is controlled to withdraw the bendable body 3 from the patient. This process is similar to the navigation process described in, e.g., US 2007/0135803, which is incorporated by reference herein for all purposes. Additional details for driving a snake-type robot include the control methods for actuation, as described in applicant's previous patent application publications US 2015/0088161, US 2018/0243900, US 2018/0311006, and US 2019/0015978, which are also incorporated by reference herein for all purposes.

<FIG. 3A-FIG. 6C: Connector Assembly and Operation Thereof>

In any of the embodiments, there is a motor or actuator that is actuating a driving wire 115 to navigate the bendable body 3 through the patient's anatomy. There can be an individual motor or actuator for each driving wire 115, or there can be a single motor or actuator that can control various (or all) driving wires 115 individually. A driving wire 115 is moved longitudinally along the length direction of the bendable body 3 (often in conjunction with other driving wires) to create a bending moment at a distal location of the instrument (catheter or endoscope). The structure of the instrument allows for one or more of these bending sections to be actuated individually. In the present disclosure, one important aspect is that regardless of the type of actuator used (DC motor, linear inductive motor, ultrasonic motor, or the like) a linear force is generated to move the driving wires individually, and such force is transferred to the driving wires with minimal losses.

In the case of a direct current (DC) rotating motor, there needs to be a transformation from rotational motion to linear motion; for this, a lead screw or a ball screw mechanism is typically used. See, for example, U.S. Pat. No. 9,629,688.

But other alternatives, such as ultrasonic and direct drive actuators, can be more advantageous. The benefit of an ultrasonic motor and of a linear inductive motor is that these are both linear actuators and do not need mechanical conversion. The ultrasonic motor or linear inductive motor can directly drive the driving wire in a linear direction without any mechanical gears or intermediate mechanisms. One benefit of directly driving the driving wires with such linear actuators is the reduction of friction and other nonlinearities (e.g. mechanical slop in a lead screw mechanism).

However, even when using a linear actuator (ultrasonic motor and of a linear inductive motor), a mechanical connection is still necessary to transfer the force from the actuation unit to the bendable body 3. In particular, since the bendable body 3 is often designed to disposable or of limited use due to sterility requirements, it is important that a user be able to quickly connect and disconnect the bendable body 3 from the actuator unit 7. As previously mentioned in the Background of present disclosure, conventional technology uses a connector cartridge or other connector structures which includes perpendicular moving directions between the driving wires and actuators of actuation unit. The driving wires are usually bent or routed through curved paths in the connection cartridge. This makes the connector assembly difficult to be miniaturized, creates relatively large loss of the driving forces, and can create backlash and/or slack in the driving wires.

Figure 3A:
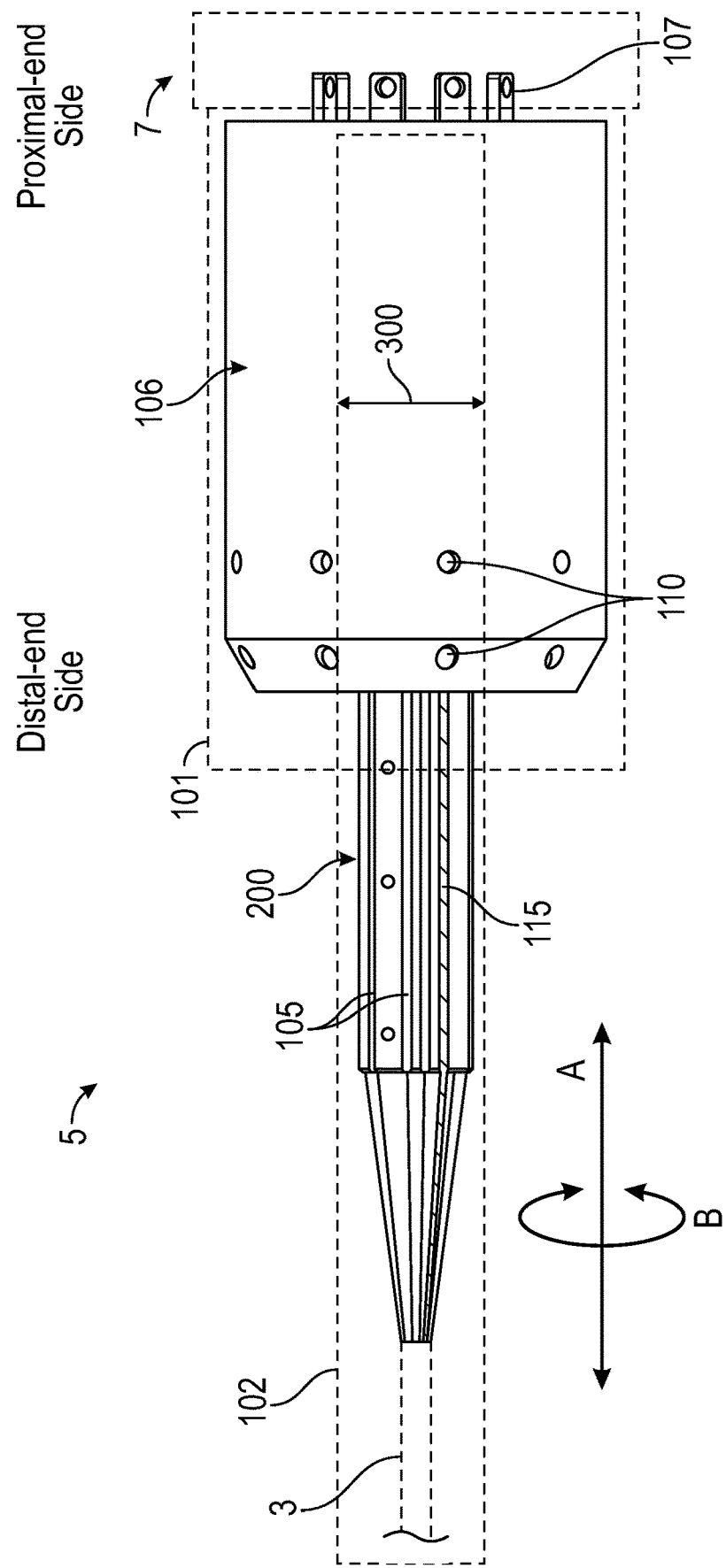
FIG. 3A and FIG. 3B illustrate an example embodiment of a connector assembly 5 that includes a connecting shaft 102 and a connection receptor 101.
Figure 3B:
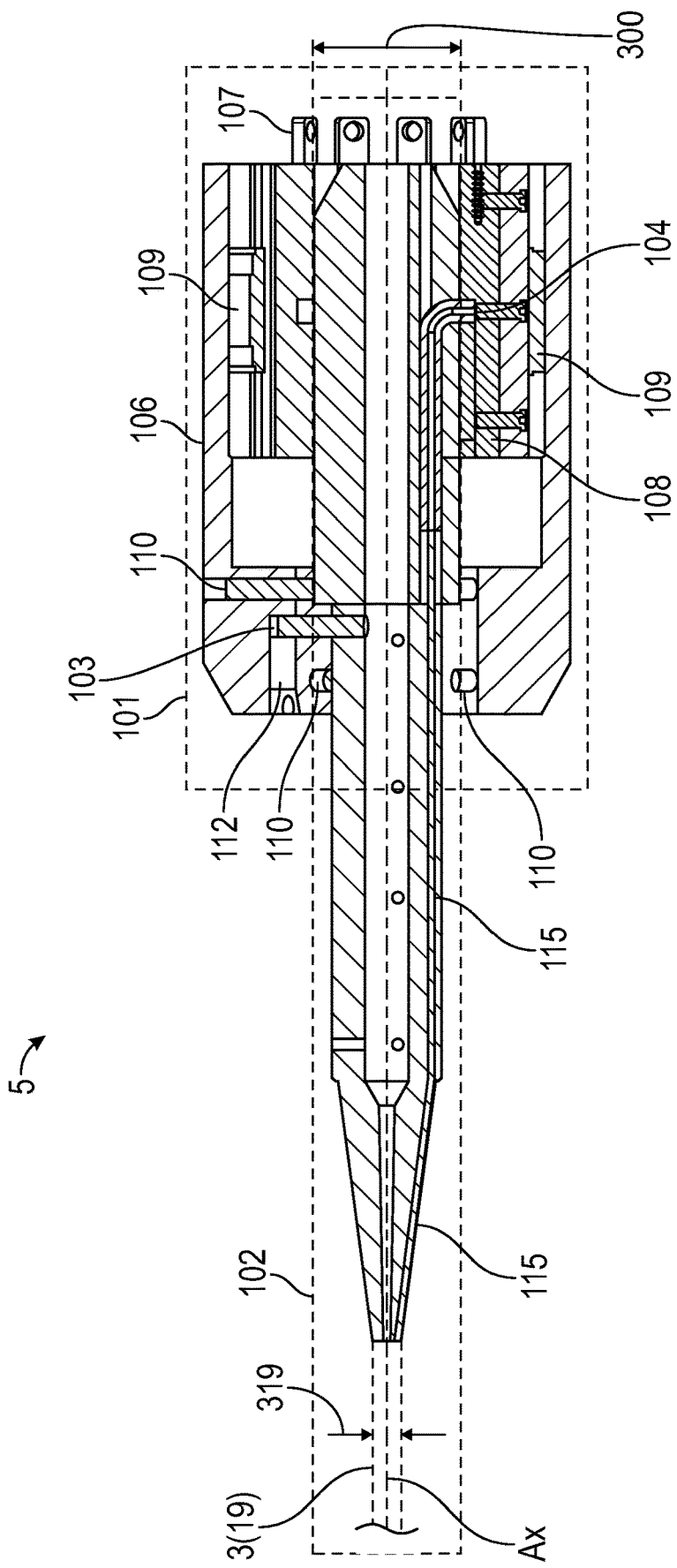

FIG. 3A and FIG. 3B illustrate an example embodiment of a mechanical connector assembly 5 configured to connect the actuation unit 7 to the bendable body 3 without loss of driving force and with a quick single action movement, according to the present disclosure. The connector assembly 5 includes a bendable-body connecting shaft 102 (connecting shaft) and a connection receptor 101. The connection receptor includes a plurality of driving stages 108 connectable to an actuation unit 7 via connecting units 107. The connecting shaft 102 includes a plurality of driving rods 104 coupled in a one-to-one correspondence with a plurality of driving wires 115. As shown in FIG. 3A-FIG. 3B, the connecting shaft 102 detachably attaches the bendable body 3 to the connection receptor 101, by engaging the driving rods 104 to the driving stages 108, in a quick action of inserting the connecting shaft 102 in a linear direction A and briefly rotating said connecting shaft 102 in a rotating direction B. In this manner, a plurality of actuators 70 arranged in the actuation unit 7 can manipulate (actuate) the bendable body 3 via the connector assembly 5 with actuation forces transmitted in a linear direction substantially without losses.

Here, the connection units 107 are a mechanism used to create a mechanical connection between each driving stage 108 and the actuator/motor of the actuation unit 7. In most embodiments, this mechanical connection would be completely rigid and made permanent during the manufacturing and assembly process. Each connection mate can be done through adhesive bonding or bolt and thread, for example.

The connecting shaft 102 has a substantially cylindrical body is configured to connect the bendable body 3 (a first bendable tubular body) to an aperture (inner opening 300) of the connector body 106 (a second non-bendable tubular body) along a common longitudinal axis (Ax). The connecting shaft 102 includes a plurality of driving rods 104 arranged around the substantially cylindrical body. The driving rods 104 include a first segment 42 and a second segment 44, the first segment 42 being longer than, and arranged at an angle with respect to, the second segment 44. When arranged on the cylindrical body of the connecting shaft 102, the second segment 44 of the driving rod 104 extends radially from the substantially cylindrical body. The connector assembly 5 also includes at least one bendable-body locking pin 103 and connecting-shaft guiding pins 110 which extend radially around the longitudinal axis and substantially perpendicular to both the connecting shaft 102 and the connection receptor 101.

Figure 5A:
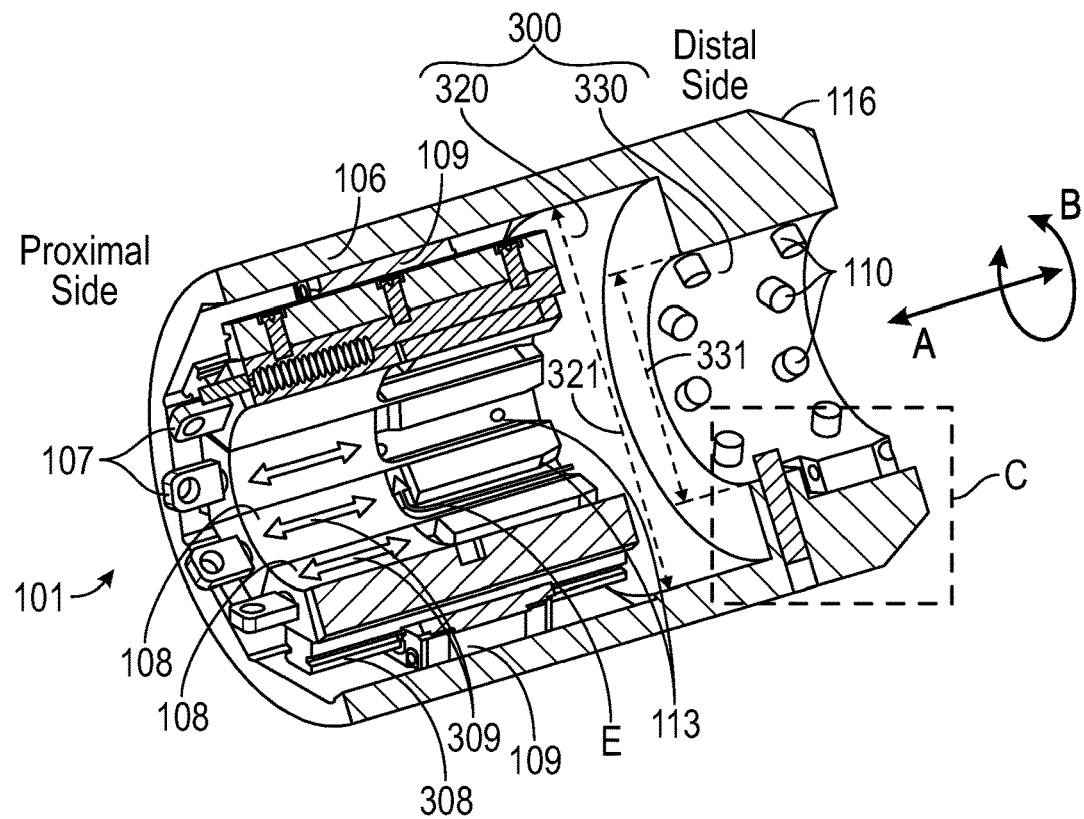
FIG. 5A illustrates an example embodiment of a connection receptor 101. FIG.
Figure 5B:
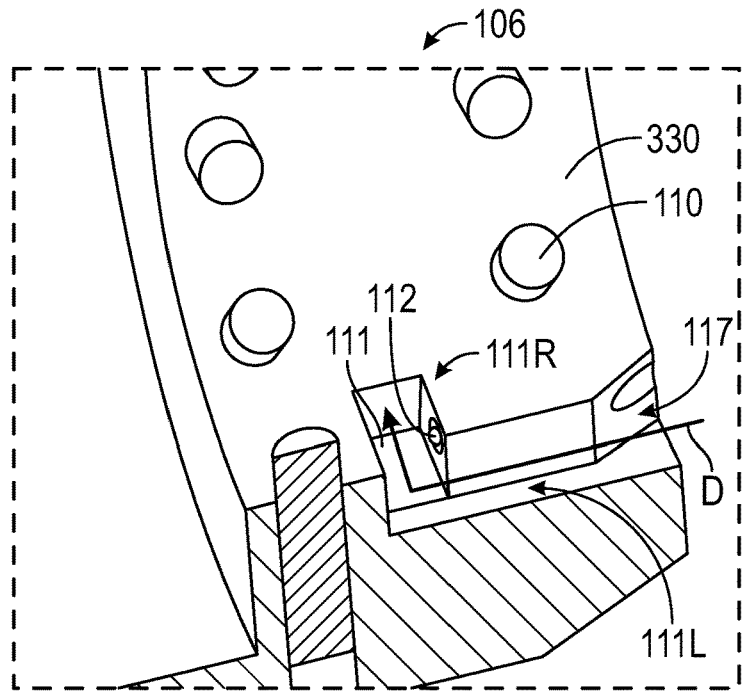
FIG. 5B illustrates is a magnified view of an area C in FIG. 5A.

FIGS. 4A and 4B illustrate further details of the bendable-body connecting shaft 102; and FIGS. 5A and 5B illustrate further details of the connection receptor 101. FIG. 4A illustrates a 3D rendering of the connecting shaft 102 according to an example embodiment of the present disclosure. FIG. 5A illustrates a 3D rendering of a portion of the connection receptor 101 according to an example embodiment of the present disclosure. As shown in FIG. 4A, the bendable-body connecting shaft 102 has a substantially cylindrical body 200 made of solid material with varying outer diameters, which change from a first outer dimeter OD1 at the proximal end thereof, to a second outer diameter OD2 in a proximal section 204, to a third outer diameter OD3 in an intermediate section 202, and a fourth outer diameter OD4 at a distal end of a distal section 201. In one example embodiment, the entire connecting shaft 102 can be made of hard plastic material by molding, 3D printing, or similar processes. In alternative embodiments, at least sections 201 and 202 of connecting shaft 102 can be made of a single plastic piece, and section 204 can be a separate plastic piece pressure fitted onto section 202. The locking pin 103 is pressed in with an interference fit. Each driving rod 104 has a longer segment 42 that slides into a guiding channel 105 with a slip fit allowing for smooth linear motion.

As shown in FIG. 3B, the bendably-body connecting shaft 102 is a proximal portion of the bendable body 3, and serves to mechanically transmit actuation forces from the actuation unit 7 to the bendable body 3. To transmit the actuation force, the connecting shaft 102 must be removably engaged with the connection receptor 101. To facilitate ease of engagement and disengagement with the connection receptor 101, and to ensure smooth transmission of the actuation force, the connecting shaft 102 is tapered at both the proximal and distal ends thereof.

First, at the proximal end of the substantially cylindrical body 220, the proximal section 204 of the connecting shaft 102 is tapered in the direction of the distal to proximal end such that the OD2 is greater than the OD1. The tapering at the proximal end is advantageous as it can allow for easy insertion of the connecting shaft 102 into the central opening 300 of the connection receptor 101. The OD2 of the proximal portion 204 is dimensioned to fit within the inner diameter 331 of the connection receptor 101. The intermediate section 202 of the connecting shaft 102 has an outer diameter OD3 which is smaller or equal to OD2. The intermediate section 202 arranges the driving wires 115 along the guide channels 105 at equal intervals (at a circular pitch CP). And, at the distal end of the cylindrical body 200, the section 201 of the connecting shaft 102 is tapered in the direction from the proximal to the distal end, such that the OD3 of intermediate section 202 tapers to the OD4, where OD4 is substantially equal to an outer diameter 319 of the bendable body 3 (shown in FIG. 3B). Tapering from OD3 to OD4 at the distal end of the connecting shaft 102 is important and advantageous to provide a smooth transition in stiffness from the connecting shaft 102 to the proximal part 19 of the bendable body 3. Since the proximal part 19 of the bendable body 3 is part of (or is rigidly connected to) the distal end of the connecting shaft 102, it is important to provide a smoot transition from the connecting shaft 102 to the small diameter 319 of the bendable body 3 to minimize the possibility of buckling of the bendable body 3.

An important aspect of tapered sections in the connecting shaft 102 is the smooth transition from the connector assembly to the bendable body 3. In particular, it is important to note that the tapered transition from OD3 to OD4 allows the drive wires 115 to transition from the small operating pitch in which they are arranged inside the bendable body 3 (catheter) to the larger pitch of the connecting shaft 102 (connection mechanism) and the actuator unit 7. This transition needs to be smooth and gradual to avoid friction loses in the drive wire and potential binding/kinking of the bendable body 3.

The bendable-body connecting shaft 102 includes two or more (a plurality of) guide channels 105 arranged lengthwise around the outer surface of the substantially cylindrical body 200 of the connecting shaft 102. Guide channels 105 are formed as grooves formed lengthwise extending from the proximal end to the distal end of the connecting shaft 102. At the proximal end of the proximal part 19, guide channels 105 are arranged with corresponding wire conduits. Each driving wire 115, from the bending sections of bendable body 3, passes through the proximal part 19, runs through a separate guide channel 105, and is terminated attached to a corresponding driving rod 104. The driving wire 115 is adhesively bonded or otherwise attached to the driving rod 104.

According to the embodiment shown in FIG. 4A, each guide channel 105 extends lengthwise from the proximal end to the distal end of the connecting shaft 102. At the proximal section 204, the guide channel 105 is made according to a shape and size (dimensions) of the driving rod 104. At the middle section 202 and tapered section 201, the guide channel 105 is made narrower and less deep to fit therein the size and shape of a driving wire 115. Each driving rod 104 mechanically connects to the proximal end of each driving wire 115. The driving rods 104 are slideable in the guide channels 105 along the direction of arrow A to pull and push the driving wires 115 for manipulating one or more bending sections of the bendable body 3. In order for the guide channel 105 to function properly, it must have a certain clearance fit relative to the driving rod 104. If the tolerance is too tight, there will be frictional loses and potential binding when driving the drive wire. If the tolerance is too loose (too tight), there will be too much play in the driving rod 104 which can lead to engagement misalignment or backlash. In an example embodiment the drive rods 104 may have an OD of 3 mm, so the guide channel 108 should have a range of approximately 3.025 to 3.08 mm. It should be understood that while the embodiments disclosed herein, show the guide channels 105 as grooves open outward, the guide channels 105 could also be formed as closed conduits or lumens, so that driving wires 115 pass through conduits, as in proximal part 19 shown in FIG. 2B.

FIG. 4B illustrates an example embodiment of a driving rod 104 configured to be securely attached to a driving wire 115, according to one embodiment. In this embodiment, the driving rod 104 has a substantially cylindrical body including a central opening 41 and extending from a distal end (first end) 40 to a proximal end (second end) 45. The driving rod 104 is formed of a first (longitudinal) segment 42, a curved segment 43, and a second (transversal) segment 44, such that the driving rod 104 is substantially L-shaped. The first longitudinal segment 42 is longer than the second transversal segment 44. The first and second segments 42 and 44 are straight or linear which are joined by the curved segment 43, such that the first and second segments are substantially perpendicular to each other. According to the embodiment of FIG. 4B, the first and second segments can be arranged at an angle of about 90-degrees with respect to each other. In other embodiments, the angle between the first and second segments can be smaller or larger than 90.

At least for some embodiments, the driving rods 104 can be made from metallic material, such as a 304 Stainless Steel tube or similar. To arrive at the desired shape, the raw tube is bent to a 90 degree angle in a press. The angle can technically be smaller or larger than 90 degrees as long as the accepting slot (driving-rod locking way 113) in the driving stage 108 matches the angle of the driving rod 104. The central opening 41 can be tailored to a diameter of the driving wire 115. In one embodiment, the outer diameter (OD) of the driving rod 104 would be roughly 3 mm with the inner opening 41 having an inner diameter (ID) of about 0.8 mm or larger if necessary for allowing additional tubes to be inserted to ultimately connect to the drive wire. Here, "additional tubes" (not shown) would serve as rigid sliding members arranged inside opening 41 to connect the large driving rod 104 (3 mm diameter) to the smaller driving wire (<0.8 mm diameter). Specifically, the additional tubes would serve as a guideway for the driving wire preventing kinking and/or slack of the drive wire. In alternate embodiments, the driving rod 104 can be made of non-metallic material (e.g., of extruded or 3D printed plastic) and can have square or rectangular shapes which can help reduce play while sliding.

The bendable-body connecting shaft 102 also includes at least one shaft locking pin 103 (a first locking pin) which serves to guide and couple (e.g., fix, attach, or connect) the connecting shaft 102 to an inner surface of the connection receptor body 106 when the connecting shaft 102 is engaged with the connection receptor 101. In one embodiment, the locking pin 103 is a cylindrical pin fixedly attached (e.g. pressure fitted) to the connecting shaft 102 such that the locking pin 103 protrudes from the outer surface thereof. For ease of manufacturing, the locking pin 103 can be a cylindrical pin substantially perpendicular to the connecting shaft 102. An important aspect of providing the locking pin 103 on the body of the connection shaft 102 is that the locking pin 103 can improve speed and accuracy of engagement because the locking pin 103 aligns and guides the connecting shaft 102 with a connecting-shaft locking way 111, as further explained below.

The locking pin 103 is an important aspect of the connector assembly as it prevents the connecting shaft 102 from coming loose from the connector receptor body 106 during a steering operation. Without the locking pin 103, the only connection being made between the connecting shaft 102 and the connector receptor 101 would be between the rods 104 and the locking ways 113. However, in that case, the connecting shaft 102 and the connector receptor 101 are not rigidly connected to each other, and there would be some undesirable play between the two components. Therefore, having the locking pin 103 creates a mate that locks the connecting shaft 102 and the connector receptor 101 in a rigid manner. It is noted that more than one locking pin 103 or an alternate locking mechanism could be used to rigidly connect the connecting shaft 102 to the connector receptor 101. In alternate embodiments, the locking pin 103 or other locking mechanism could be provided in the inner surface of the connection receptor 101, as long as such locking mechanism can rigidly lock the connecting shaft 102 and the connector receptor 101 together. For example, a locking pin 103 with a spring plunger can be provided on the inner surface 330 of the connector receptor body 106.

In some embodiments, the connecting shaft 102 includes expansion units (not shown), such as the expansion units described in PCT Publication WO 2018/204202, which is hereby incorporated by reference in its entirety. The expansion units include break-out wires that can attach to the driving wires 115 and a contracting guide that is movable with respect to the driving wires 115. The expansion unit allows for the expansion of a wire diameter from, for example, a very small driving wire suitable for use within a small catheter device to a driving wire with a larger diameter that is more suitable for connecting to the connection receptor 101.

FIG. 5A illustrates an example embodiment of a connection receptor 101; and FIG. 5B illustrates a magnified view of an area C of FIG. 5A. As shown in FIG. 5A and FIG. 3A, the connection receptor 101 includes a connector body 106 which is substantially cylindrical in shape and has a central opening 300 configured to receive therein the connecting shaft 102. The central opening 300 has, in an order from the proximal-end side to a distal-end side, a first inner surface 320 having a first diameter (ID1) 321 and a second inner surface 330 having a second diameter (ID2) 331, where the second diameter (ID2) 331 is smaller than the first diameter (ID1) 321.

On the proximal-end side, the connector body 106 has a plurality of controller-connecting units 107 (connecting units) configured to connect the connecting shaft 102 to the actuation unit 7 so as to transfer actuation force therebetween. On the distal-end side, a part 116 of the outer surface of the connector body 106 is tapered in the proximal to the distal direction. A plurality of driving stages 108 (driving stages) are arranged in a circular fashion around the first inner surface 320 of the cylindrical opening 300. Each driving stage 108 is arranged on a linear rail 308 and is operatively coupled to a linear slider 109, such that each driving stage 108 moves in a linear direction 309 upon receiving the actuation force from the actuation unit 107. Each driving stage 108 provides a driving-rod locking way 113 (a first locking way) which serves to receive therein a portion of a corresponding driving rod 104 arranged on the connecting shaft 102. The plurality of linear sliders 109 are provided in a one-to-one correspondence to the number of driving stages 108. On the second inner surface 330, a plurality of shaft guiding units 110 (guiding pins), and at least one shaft locking way 111 (a second locking way) are provided. A spring plunger 112 located adjacent to the locking way 111 serves to engage the bendable-body locking pin 103 provided on the bendable-body connecting shaft 2 to secure a position of the connecting shaft 102 with respect to the connection receptor 101.

FIG. 3B shows an example embodiment of the connecting shaft 102 engaged with (or coupled to) the connection receptor 101. In operation, when the bendably-body connecting shaft 102 is engaged with the connection receptor 101, the connecting shaft 102 is inserted into the central opening 300 of the connection receptor 101 in a direction from the distal end towards the proximal end as shown by arrow A, and is then quickly rotated along a direction of arrow B. As a result, the bendable-body locking pin 103 of the connecting shaft 102 is engaged with the locking way 111. To engage with the locking way 111, in a push (linear) motion, the bendable-body locking pin 103 first aligns with a chamfered edge 117, then slides along a longitudinal part 111L of the locking way 111 in the direction along arrow A. Then, in a rotating action along direction of arrow B, the locking pin 103 turns in the direction of arrow D (see FIG. 5B) and slides into a transversal part 111R of the locking way 111. Once the locking pin 103 is in position, the locking ping 103 is pressed and fixed by the spring plunger 112 which abuts against the locking pin 103. To disengage from the connection receptor 101, the connecting shaft 102 is first rotated in a twist motion and then pulled in a linear direction from the proximal toward the distal end.

During the engagement action, the connecting shaft 102 is also guided with one or more shaft guiding units 110 provided near (in the vicinity of) the locking way 111 in the distal-end side of the connection receptor 101. In this example embodiment of FIG. 5A-5B, the shaft guiding units 110 are cylindrical pins arranged circumferentially along the inner surface 330 (the second inner surface) of the connection body 106. These guiding units 110 can be made with a material that has low friction or with an appropriate amount of self lubricant material to facilitate manual sliding action of the bendable-body connecting shaft 102 with the connection receptor 101. The shaft guiding units 110 are configured to align the position of the connecting shaft 102 with respect to the connection receptor 101 for consistent and secure engagement. As it can be understood from FIG. 4A, the tapered section at the proximal end of the connecting shaft 102 ensures easy alignment of the shaft guiding units 110 with the outer surface of the connecting shaft 102.

Figure 6A:
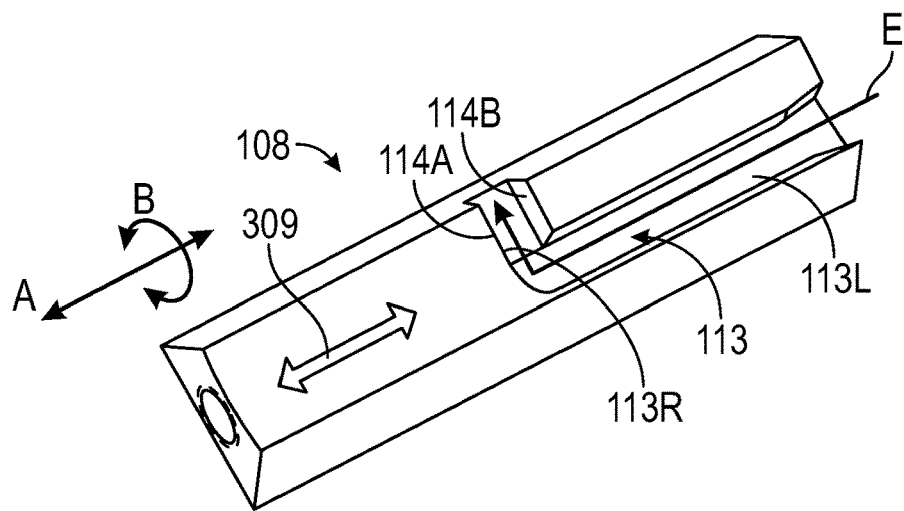
FIG. 6A illustrates an example embodiment of a driving stage 108.

When the connecting shaft 102 is being engaged with the connection receptor 101, each of the driving rods 104 advances along a longitudinal part of a respective locking way 113 in each driving stage 108 in the direction of arrow A, and, subsequently, each of the driving rods 104 seamlessly rotates circumferentially to a position between respective locking facets 114A and 114B of the locking way 113 in the direction of arrow B. FIG. 6A illustrates an example embodiment of a driving stage 108 having an L-shaped locking way 113. As shown in FIG. 6A, the locking facets 114A and 114B can fix the position of the driving rod 104, and allow actuation thereof with the linear movement of the driving stage 108 along a linear direction 309.

The driving stages 108 are connected to and moved by actuators or motors in the actuation unit 7 via a plurality of actuator connecting units 107. When moved by the motors, the driving stages 108 move the driving rods 104 independently from each other. The driving rods 104, in turn, transfer the actuation force to move the driving wires 115 and to bend a corresponding bending section in the bendable body 3.

Because the driving wires 115 and the driving stages 108 have the same driving directions (linear driving directions), the bendable-body connector assembly 5 can transfer the driving forces with minimal losses, and a size of connector receptor 101 can be minimized with a minimal space to configure shaft engagement and movement for force transmission.

Moreover, the driving rods 104 and L-shaped driving-rod locking ways 113 create rotational actions to engage all driving wires 115, and simultaneously a rotational action also engages the shaft locking pin 103 with the L-shaped locking way 111, with a simple user maneuver. That is, the same action of linear movement in direction A and rotation in direction B simultaneously engages the connecting shaft 102 and the driving rods 104 with the connector receptor 101. In addition, because the rotational action of engagement is substantially perpendicular to the driving direction (movement linear direction 309) of the driving wires 115 and driving rods 104, the bendable body 3 can be protected from an unexpected large force of engagement.

Also, the L-shaped driving-rod locking ways 113 can easily adjust the positions of the L-shaped driving rods 104 to the proper initial positions when they are initially engaged to their respective driving stages 108. For example, when the bendable body 3 accidentally bends prior to being connected to the actuation unit 7, the engagement action can quickly adjust the positions of the driving wires 115 to positions corresponding to a home position of the L-shaped locking ways 113, which can be consistently initialized with actuators by sliding the driving stages 8 to a same longitudinal position, e.g., as shown in FIG. 5A.

As previously discussed, there is often a concern that backlash may remain in the connection mechanism between the driving rod 104 and the locking way 113. In the case that backlash does become an issue in the connection of the driving rod to the locking ways, certain modifications to the above discussed designs of the connector assembly can further reduce slack and therefore avoid backlash, as explained below.

It is understood that a steerable medical device having a bendable body 3 requires rigid, high bandwidth connection between the actuator and the payload. To elaborate on what it means to have a high bandwidth system, when the actuator initiates motion, the motion should be of the same magnitude and instantaneous at the payload. However, in the event where the connection between the actuator and the payload is not completely rigid, there can be a loss of magnitude and delay of actuation in the system. Backlash could exacerbate the situation in a system where continuous push/pull actuation is necessary for accurate navigation. With backlash, bidirectional error could be introduced into the system. In this case, backlash also creates an issue with the force feedback mode which constantly relies on high bandwidth tracking between the actuator and the payload. Furthermore, with backlash it becomes difficult for the force sensors to pick up on loads that the drive wires face since such forces would be absorbed by the deflection in the backlash.

In the design of the connector assembly shown in FIG. 3A-6A, connection is made by sliding a bent (L-shaped) driving rod 104 into a curve (L-shaped) locking way 113. In order for this action to happen quickly and comfortably for the user, there must be a clearance between the outer diameter of the driving rod 104 and the width (diameter) of the locking way 113. Without a clearance (or tolerance) to fit each driving rod 104 into the corresponding locking way 113, it would require high precision alignment and possibly high torque from the user. This alignment precision would be difficult to achieve by the user, in particular when considering that a plurality of driving rods 104 (for example 9 rods) would need to simultaneously line up with their respective slots of locking ways 113.

Figure 6B:
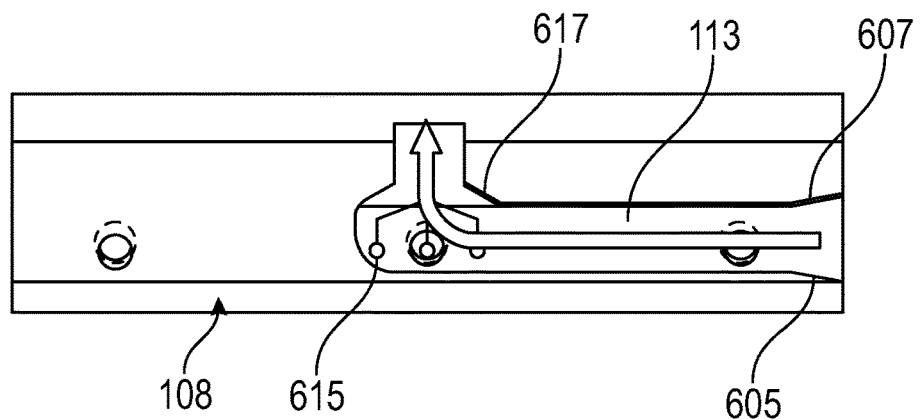
FIG. 6B illustrates an example embodiment of a driving stage 108 with a locking way 113 having chamfered edges.

In the present disclosure, to provide a certain degree of clearance for the driving rods 104, the locking ways 113 of each driving stage 108 are formed with chamfered edges. FIG. 6B illustrates an example embodiment of a driving stage 108 configured to provide a desired degree of tolerance. As mentioned above, the design of connector assembly 5 requires that all driving rods 104 (e.g., 9 driving rods in one embodiment) should be perfectly lined up with the locking ways 113 or else it will be difficult for the user to engage the connecting shaft 102 with the connection receptor 101. Without any additional mechanism introduced to the design, there could be chances of the connection receptor 101 failing to engage with the connecting shaft 102 or that the binding forces are too high. One way to alleviate this difficulty is to introduce chamfers at the entrance of the locking ways 113 that will accept the driving rods 104 at varying positions. FIG. 6B shows one example embodiment of a driving stage 108 where the locking way 113 has chamfered edges 605 and 607 at the entrance of the L-shaped slot or groove. In addition, chamfered edges 615 and 617 are provided at the curved part of the L-shaped locking way 113 to allow some clearance for the driving rod 104 to easily turn and lock in position. Therefore, as the user inserts (pushes) and twists the connecting shaft 102 inside the connection receptor 101, the chamfered edges at the entrance of each locking way 113 guide the driving rods 104 into place.

Figure 6C:
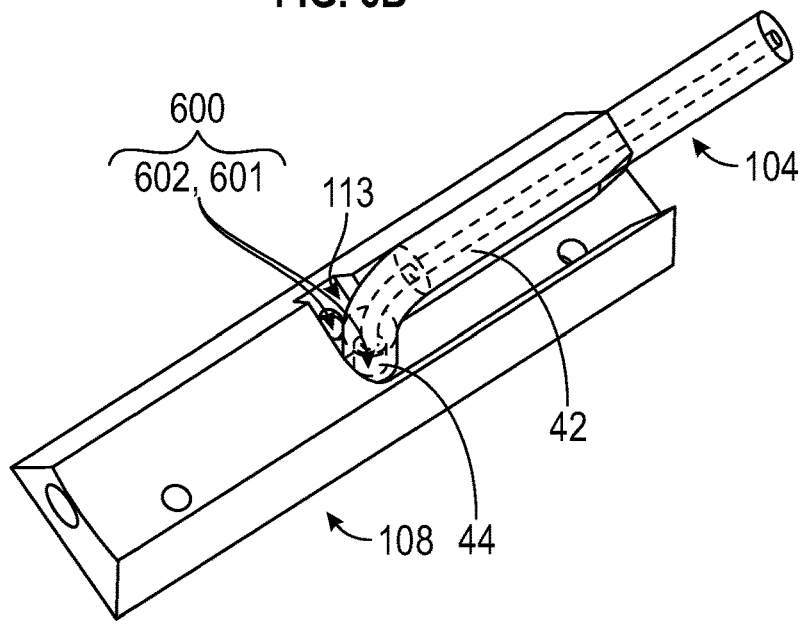
FIG. 6C illustrates an example embodiment of a driving stage 108 with a driving-rod locking mechanism for magnetic coupling to a driving rod 104.

However, as noted above, this added tolerance provided by the chamfered surfaces and other manufacturing and assembling tolerances would result in a certain degree of slack and/or backlash. According to the present disclosure, backlash can be eliminated by adding individual locking mechanisms that clamp the driving rods 104 into place so there is no motion (no slack) between the slot of the locking way 113 and the driving rod 104. This locking mechanism for securing each driving rod 104 to the locking way 113 is referred to as a driving-rod locking mechanism and can be implemented through several mechanisms. FIG. 6C illustrates an example embodiment of a driving stage 108 with a magnetic coupling mechanism 600 for securing a driving rod 104 to a predetermined position. According to the example embodiment shown in FIG. 6C, a pair of attracting magnets including a first magnet 601 in the driving rod 104 and a second magnet 602 in the slot of locking way 113 are provided. As described above, the driving rod 104 can be an L-shaped rod having a second segment 44 substantially perpendicular to a first segment 42. The first magnet 601 can be embedded in the tip of second segment 44, and the second magnet 602 can be embedded in the transversal slot of the locking way 113. During engagement of the connecting shaft 102 with the connection receptor 101, as the connecting shaft 102 moves in the direction of arrows A and then B (see FIG. 6A), the second segment 44 sits and is held within the transversal slot of locking way 113. At this point, the second magnet 602 located in the locking way 113 attracts the first magnet 601 located in the second segment 44 of driving rod 104. In this manner, the driving rod 104 can be locked into a specific position relative to the slot.

The same effect can be achieved with a locking mechanism made of a spring and latch based mechanism. Therefore, the driving rod 103 could also be locked in a specific position with a spring plunger 112 as shown in FIG. 5B. In both cases these mechanisms would be passive in a sense where they engage with minimal torque from the user and disengage with a significant but reasonable amount of torque. This means the disengagement force and torque would be high enough to tolerate outside noise during operation but low enough for user comfort. The appropriate force and torque could be designed by varying the size of the spring and/or magnet used in the locking mechanism.

An alternative approach for eliminating backlash is to program backlash compensation into the control software. This approach however would not fully solve this issue due to manufacturing tolerance variations between parts. That is, in the case of using software-based backlash compensation, there would still remain a certain degree of error equivalent to the tolerance range specified.

Referring back to FIG. 4A it can be understood that at least one example embodiment of the connecting shaft 102 includes a plurality of guide channels 105 arranged lengthwise on the outer surface of a substantially cylindrical body. These guide channels 105 provide a linear guide for movement of L-shaped driving rods 104 and drive wires 115 attached thereto. Each driving wire 115 is mechanically attached or adhesively bonded to a driving rod 104. In turn, each driving rod 104 also radially protrudes from the cylindrical body and is locked in a locking way 113 of a driving stage 108 (not shown). Mechanical connecting units 107 physically link an actuator 70 to a driving stage 108 and thus to the driving rod 104. Since the connecting shaft 102 tapers in a section 201 (from OD3 to OD4) to provide a gradual and easy transition of driving forces from the actuators 70 to the bendable body 3, the actuating force is transmitted with minimal mount of losses.

More specifically, in this example embodiment of FIG. 4A, it can be appreciated that generated actuating forces from the actuators 70 (see FIG. 1B) can be transmitted to the bendable body 3 in the same direction and substantially the same magnitude as transmitted from the actuation unit 7. A minimal amount of actuating force can be considered to be lost due to a change in diameter when transferring from the outer diameter of the connecting shaft 102 to the dimeter of the bendable body 3. However, this loss is minimized by the smooth tapering of section 201 of the connecting shaft 102. According to one example embodiment, the tapering section 201 can have a length (37.67 mm) which is approximately half the length (75 mm) of the non-tapered sections 202+204 of the connecting shaft 102. This structure makes it clear that the bent (L-shaped) driving rod allows for minimal losses of force in the translation of the driving wire itself. Since the actuator motion is parallel to the driving wire motion (i.e., the actuation force is the same direction as, or parallel to, the driving force), there is minimal frictional loss that occurs. This is in direct contrast to conventional systems (e.g., U.S. Pat. No. 9,629,688 B2) in which the actuation motion is perpendicular to the driving wire motion/force.

Also, some embodiments of a medical robotic system comprise a bendable-body assembly, an actuation unit, an insertion unit, and a controller. The bendable-body assembly includes a bendable body, a driving wire, a bendable-body locking pin, and a connection receptor. The bendable body is configured to bend at one or more bending sections upon receiving an actuation force. The actuation unit is detachably connected to the bendable-body assembly via the connection receptor and is configured to generate the bending force to bend the bendable body. The controller is configured to control the actuation. The driving wire has an L-shaped driving rod at the proximal end. The driving rod has a first segment which slides along a guiding channel formed on the connecting shaft of the bendable body assembly, and second segment which extends in a radial direction from a centroid of the bendable-body assembly.

The connection receptor, which connects the bendable-body assembly to the actuation unit, includes an L-shaped driving-rod locking way and an L-shaped shaft locking way. The driving rod is configured to engage at least one of two sides in the L-shaped driving-rod locking way with a rotational motion. Also, the L-shaped shaft locking way of the connection receptor and the body-locking pin of the bendable-body assembly are engaged with the rotational motion.

Also, some embodiments of a bendable-body assembly comprise a bendable body, a driving wire, a connecting shaft, and a connection receptor. The connecting shaft includes a linear channel guide and a driving rod that is attached to the driving wire; the driving rod moves linearly along the linear channel guide and extends radially from the connecting shaft. The connection receptor includes a connection-receptor body having a central opening that is configured to receive therein the connecting shaft. The connection-receptor body includes a driving stage with a corresponding a linear slider. The driving stage includes a driving-rod locking way. The driving rod is configured to engage the driving-rod locking way with a rotational motion. The driving stage and the linear slider are configured to allow the driving stage to move in a direction parallel to a longitudinal axis of the connection receptor.

OTHER EMBODIMENTS OR MODIFICATIONS

In referring to the description, specific details are set forth in order to provide a thorough understanding of the examples disclosed. In other instances, well-known methods, procedures, components and circuits have not been described in detail as not to unnecessarily lengthen the present disclosure. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

While the present disclosure has been described with reference to exemplary embodiments, it is to be understood that the present disclosure is not limited to the disclosed exemplary embodiments. The scope of the following claims is to be accorded the broadest interpretation so as to encompass all such modifications and equivalent structures and functions.

What is claimed is:

1. A connector assembly configured to transfer actuating forces from an actuation unit to a bendable body of a robotically steerable instrument, the bendable body having one or more bending sections, and the connector assembly comprising:
   a connection receptor operatively coupled to the actuation unit and having a substantially cylindrical opening, wherein one or more locking ways are formed on a cylindrical inner surface of the cylindrical opening; and
   a bendable-body connecting shaft having a cylindrical outer surface and configured to detachably engage and disengage the bendable body to and from the actuation unit,
   wherein the bendable-body connecting shaft includes a guide channel formed in the cylindrical outer surface and configured to guide a driving rod operatively connected to a driving wire which actuates at least one bending section of the bendable body,
   wherein the driving rod has a first segment and a second segment rigidly connected to each other at an angle, the first segment attached to the driving wire and aligned in a lengthwise direction of the bendable-body connecting shaft, and the second segment protruding radially outwards from the cylindrical outer surface of the bendable-body connecting shaft,
   wherein, in an engaged state in which the actuation unit applies an actuating force having a predetermined direction to the bendable body, the second segment of the driving rod is engaged with a first locking way of the connection receptor so that the driving rod moves the driving wire to pull or push the driving wire in a same direction as the actuating force applied by the actuation unit, and
   wherein, in the engaged stated, the second segment of the driving rod is engaged with a locking way formed in the cylindrical inner surface of the connection receptor and the second segment of the driving rod radially protrudes from the cylindrical outer surface of the connecting shaft and extends through the inner cylindrical surface of the cylindrical opening into the locking way.

2. The connector assembly according to claim 1,
   wherein the connection receptor includes a driving stage configured to move in a linear direction which is the same direction as, and parallel to, the actuating force applied by the actuation unit, and
   wherein the driving stage includes the first locking way to which the second segment of the driving rod is engaged.

3. The connector assembly according to claim 2,
   wherein the first locking way included in the driving stage is L-shaped, and
   wherein the L-shaped locking way includes chamfered edges configured to guide the second segment of the driving rod when the bendable-body connecting shaft engages to or disengages from the connection receptor.

4. The connector assembly according to claim 2,
   wherein the bendable-body connecting shaft further includes a guide channel arranged in a lengthwise direction and configured to guide in the lengthwise direction the first segment of the driving rod that is attached to the driving wire.

5. The connector assembly according to claim 2,
   wherein the driving stage includes a first magnet arranged in the first locking way,
   wherein the second segment of the driving rod includes a second magnet, and
   wherein, in the engaged state in which the actuation unit applies an actuating force having a predetermined direction and magnitude to the bendable body, the second magnet is configured to magnetically attract the first magnet to prevent the driving rod from moving away from a predetermined position.

6. The connector assembly according to claim 2,
   wherein the connection receptor further includes a plurality of guiding pins that are arranged radially around the cylindrical inner surface of the cylindrical opening and that are configured to position and guide the bendable-body connecting shaft into the cylindrical opening of the connection receptor.

7. The connector assembly according to claim 6,
wherein the bendable-body connecting shaft further includes a locking pin,
wherein the connection receptor further includes a second locking way arranged in the inner surface of the cylindrical opening and configured to receive therein the locking pin,
wherein the locking pin of the bendable-body connecting shaft is configured to engage with the second locking way of the connection receptor with a rotational motion of the connecting shaft relative to the connection receptor, and
wherein the driving stage is configured to engage the second segment of the driving rod with the rotational motion of the bendable-body connecting shaft relative to the connection receptor.

8. The connector assembly according to claim 2,
wherein the driving stage includes an actuator attachment unit configured to mechanically connect the driving stage to an actuator of the actuation unit.

9. A system for controlling a robotically steerable apparatus, comprising:
a bendable body having an outer surface and an inner surface defining a wall, the inner surface defining at least one tool channel and the wall having a plurality of wire conduits in a lengthwise direction of the bendable body;
a plurality of driving wires, each positioned to slidingly move lengthwise along the wall of the bendable body within a corresponding wire conduit;
a connector assembly configured to detachably connect the bendable body to an actuation unit; and
a controller configured to control the actuation unit,
wherein the connector assembly comprises: a connection receptor coupled to the actuation unit, and a connecting shaft coupled to the bendable body,
wherein the connection receptor has a cylindrical inner surface configured to hold a plurality of driving stages arranged in a circular fashion around the cylindrical inner surface,
wherein the connecting shaft has a cylindrical outer surface and is configured to engage with the connection receptor to transfer an actuation force from the actuation unit to the bendable body,
wherein the connecting shaft includes a plurality of guide channels formed in the cylindrical outer surface thereof, and the plurality of guide channels are configured to guide a plurality of driving rods that are attached in a one-to-one correspondence to the plurality of driving wires,
wherein the plurality driving rods are positioned in a one-to-one correspondence in the plurality of guide channels to slidingly move lengthwise along the cylindrical outer surface of the connecting shaft and along the cylindrical inner surface of the connection receptor,
wherein, in a connected state where the bendable body is connected to the actuation unit via the connector assembly, the controller causes the actuation unit to transmit the actuating force from an actuator to a driving rod, and the driving rod actuates or moves a driving wire in a same direction as, and parallel to, the actuating force applied by the actuator, and
wherein, in the connected stated, the second segment of each driving rod is engaged with a locking way formed in the cylindrical inner surface of the connection receptor and the second segment of each driving rod radially protrudes from the cylindrical outer surface of the connecting shaft and extends through the inner cylindrical surface of the cylindrical opening into each locking way.

10. The system according to claim 9,
wherein the connecting shaft includes a shaft-locking pin which protrudes radially from the connecting shaft and substantially perpendicular to the outer surface thereof,
wherein the connection receptor includes a central opening with a plurality of locking ways formed on the inner surface of the connection receptor, and
wherein the connecting shaft is connectable to and disconnectable from the connection receptor, by guiding the shaft-locking pin along a first locking way.

11. The system according to claim 10,
wherein shaft-locking pin is a cylindrical pin, and the first locking way is an L-shaped locking way, and
wherein the connecting shaft is connectable to the connection receptor by guiding the shaft-locking pin along the L-shaped locking way in a push and twist motion.

12. The system according to claim 11,
wherein the connecting shaft is disconnectable from the connection receptor by guiding the shaft-locking pin along the L-shaped locking way in a twist and pull motion.

13. The system according to claim 9,
wherein the connecting shaft includes a plurality of guide channels formed lengthwise around the outer surface thereof,
wherein the guide channels are substantially evenly distributed around the cylindrical outer surface and substantially concentric with a longitudinal axis of the connecting shaft, and
wherein a proximal part of each guide channel is configured to receive therein a driving rod and a distal part of each guide channel is configured to receive therein a driving wire.

14. The system according to claim 9,
wherein the connecting shaft is tapered in at least one of a distal to proximal direction and a proximal to distal direction,
wherein the connecting shaft has, in a direction from the proximal end to the distal end, a first outer diameter OD1, a second outer diameter OD2, a third outer diameter OD3, and a fourth outer dimeter OD4, and
wherein the connecting shaft is tapered in a proximal section thereof from the distal to proximal direction such that OD2>OD1, in a distal section thereof in the proximal to distal direction such that OD4<OD3, and in a mid-shaft section thereof has a diameter where OD3≤OD2.

15. The system according to claim 14,
wherein the connection receptor has an opening which extends lengthwise from a proximal-end side to a distal-end side, and the opening is configured to receive therein the connecting shaft which is inserted in a linear direction from the distal-end side towards the proximal-end side,
wherein the connection receptor includes, in order from the proximal-end side to the distal-end side of the opening, a first inner surface configured to receive at least part of the proximal section of the connecting shaft, and a second inner surface configured to receive therein at least part of the mid-shaft section of the connecting shaft, and wherein the connection receptor incudes the first locking way and a plurality of guiding pins arranged in the second inner surface of the opening, and a plurality of second locking ways arranged in the first inner surface.

16. The system according to claim 15,
wherein the guiding pins are arranged radially with respect to a longitudinal axis of the substantially cylindrical opening such that the guiding pins extend substantially perpendicular to the second inner surface, and the guiding pins are configured to contact an outer surface of the substantially cylindrical body of the connecting shaft so as to align a longitudinal axis of the connecting shaft with the axis of the substantially cylindrical opening.

17. The system according to claim 16,
wherein the connection receptor incudes a plurality of driving stages each arranged on a guiding rail on the first inner surface of the substantially cylindrical opening substantially concentric with the axis of the substantially cylindrical opening, and
wherein the driving stages are configured to engage with the driving rods and independently move the driving rods in a direction substantially parallel to the axis of the cylindrical opening.

18. The system according to claim 17,
wherein each of the driving stages includes a second locking way and a driving-rod slider,
wherein the second locking way is an L-shaped locking way with chamfered edges configured to engage with the driving rod,
wherein the connecting shaft is connectable to the connection receptor by guiding the driving rod along the second locking way in a push and twist motion, and
wherein the connecting shaft is disconnectable from the connection receptor by guiding the driving rod along the second locking way in a twist and pull motion.

19. The system according to claim 9,
wherein each driving rod has a first segment and a second segment arranged substantially perpendicular with respect to each other, the first segment attached to a driving wire and aligned in a lengthwise direction of the connecting shaft and the second segment extending radially outwards from the cylindrical outer surface of the connecting shaft, and
wherein, in the connected state, the first segment of the driving rod transfers the actuating force from the actuator to the driving wire, and the second segment of the driving rod engages with a second locking way of the connection receptor.

20. The system according to claim 19,
further comprising a driving-rod locking mechanism configured to lock the second segment of each driving rod to each second locking way,
wherein the driving-rod locking mechanism incudes a first magnet included in the second segment of each driving rod, and a second magnet embedded in each second locking way at a predetermined position thereof.

21. The system according to claim 20,
wherein the second magnet is configured to attract the first magnet to prevent the driving rod from moving away from the predetermined position.

22. A connector assembly configured to removably connect a robotically steerable instrument with an actuation unit, the connector assembly comprising:
a connecting shaft which is attached to a proximal end of a bendable body of the robotically steerable instrument, the connecting shaft comprising a plurality of driving rods that are arranged radially around a cylindrical outer surface of the connecting shaft in a one-to-one correspondence with a plurality of driving wires, wherein the bendable body has an outer surface and an inner surface defining a wall, the inner surface defining at least one tool channel and the wall having a plurality of wire conduits in a lengthwise direction of the bendable body, and wherein each of the plurality of driving wires is positioned to slidingly move lengthwise along the wall within a corresponding wire conduit; and
a connection receptor that is connected to the actuation unit and includes a plurality of driving stages arranged lengthwise in a cylindrical inner surface and around an axis of a substantially cylindrical opening of the connection receptor,
wherein, in an engaged state in which the connecting shaft is engaged with the connection receptor, the plurality of driving rods is engaged in a one-to-one correspondence with the plurality of driving stages arranged on the cylindrical inner surface of the connection receptor such that the driving rods radially protrude from the cylindrical outer surface of the connecting shaft and extend through the inner cylindrical surface of the cylindrical opening into the driving stages,
wherein each of the driving stages is configured to be independently moved lengthwise along the cylindrical inner surface parallel to the axis of the substantially cylindrical opening by an actuating force applied by the actuation unit, the actuating force having a predetermined direction and magnitude, and
wherein, in response to the actuating force applied by the actuation unit, each driving stage independently moves along the cylindrical inner surface of the connection receptor and drives a driving rod to push or pull a corresponding driving wire parallel to and in the same predetermined direction and at substantially the same magnitude as the actuating force applied by the actuation unit.

23. The connector assembly according to claim 22,
wherein each of the driving stages includes a locking way with chamfered edges and with a locking mechanism, such that each locking way is configured to guide and lock a driving rod,
wherein each of the driving rods includes a first end which is attached to a driving wire and a second end which is configured to be guided with and locked by a locking way,
wherein the connecting shaft is rotatably connectable to the connection receptor, by simultaneously engaging the driving rods to the driving stages with a push and twist action, and
wherein the connecting shaft is rotatably disconnectable from the connection receptor, by simultaneously disengaging the driving rods from the driving stages with a twist and pull action.

24. The connector assembly according to claim 23,
wherein the second ends of the driving rods arranged radially around the cylindrical outer surface of the connecting shaft are configured to be independently driven by the driving stages arranged radially around the cylindrical inner surface of the connection receptor, and
wherein, in an engaged state in which each driving rod is engaged and locked by each locking way, the locking mechanism of each locking way locks the second end of each driving rod to prevent slack or backlash in each driving wire.

25. A system, comprising:
an actuation unit, a steerable instrument, and a connector assembly, wherein the connector assembly is configured to couple and uncouple the steerable instrument to and from the actuation unit in a linear and rotational motion;
the actuation unit comprising: a first actuator, and a second actuator;
the steerable instrument comprising a bendable body having one or more bendable segments, the bendable body having an outer surface and an inner surface defining a wall, the inner surface defining at least one tool channel and the wall having a plurality of driving wires arranged in wire conduits in a lengthwise direction of the bendable body;
the connector assembly comprising: a connector housing attached to the actuation unit, and a connecting shaft attached to a proximal end of the bendable body;
the connector housing having a cylindrical inner surface and comprising a linearly translating first driving stage coupled to the first actuator, and a linearly translating second driving stage coupled to the second actuator; and
the connecting shaft having a cylindrical outer surface and comprising:
  a first driving rod attached to a first driving wire, and a second driving rod attached to a second driving wire,
  the first driving rod comprising a first segment and a second segment substantially perpendicular to each other, the first segment of the first driving rod being coupled to the first driving wire, and the second segment of the first driving rod protruding radially from the cylindrical outer surface of the connecting shaft and extending into the cylindrical inner surface of the connector housing so as to couple with the linearly translating first driving stage, and
  the second driving rod comprising a first segment and a second segment substantially perpendicular to each other, the first segment of the second driving rod being coupled to the second driving wire, and the second segment of the second driving rod protruding radially from the cylindrical outer surface of the connecting shaft and extending into the cylindrical inner surface of the connector housing so as to couple with the linearly translating second driving stage;
wherein, in a state where the steerable instrument is coupled to the actuation unit, the linearly translating first driving stage is disengageably mated with the second segment of the first driving rod, and the linearly translating second driving stage is disengageably mated with the second segment of the second driving rod, such that the linearly translating first driving stage and the linearly translating second driving stage independently transmit an actuation force received from the first actuator and second actuator, respectively, to the first driving wire and the second driving wire in a same direction and at substantially the same magnitude as the actuation force received the from the first actuator and second actuator, respectively, and
wherein, in the state where the steerable instrument is coupled to the actuation unit, the second segment of the first driving rod and the second segment of the second driving rod are respectively engaged with the linearly translating first driving stage and the linearly translating second driving stage which are arranged in the cylindrical inner surface of the connector housing such that the first and second driving rods radially protrude from the cylindrical outer surface of the connecting shaft and extend through the cylindrical inner surface of the connector housing respectively into the linearly translating first driving stage and the linearly translating second driving stage.

* * * * *